United States Patent
Reich et al.

(10) Patent No.: US 6,462,069 B2
(45) Date of Patent: Oct. 8, 2002

(54) COMPOUNDS, PHARMACEUTICAL COMPOSITIONS, AND METHODS FOR INHIBITING PROTEIN KINASES

(75) Inventors: Siegfried Heinz Reich, Solana Beach; Michael B. Wallace, San Diego, both of CA (US)

(73) Assignee: Agouron Pharmaceuticals, Inc., La Jolla, CA (US)

( * ) Notice: Subject to any disclaimer, the term of this patent is extended or adjusted under 35 U.S.C. 154(b) by 0 days.

(21) Appl. No.: 09/835,566

(22) Filed: Apr. 17, 2001

(65) Prior Publication Data

US 2002/0006952 A1 Jan. 17, 2002

Related U.S. Application Data

(60) Provisional application No. 60/197,862, filed on Apr. 18, 2000.

(51) Int. Cl.$^7$ .................. A61K 31/4155; C07D 409/04
(52) U.S. Cl. ................. 514/407; 548/364.4; 548/364.7; 548/365.7; 546/275.4; 514/341
(58) Field of Search .............................. 514/407, 341; 548/364.4, 364.7, 365.7; 546/275.4

(56) References Cited

U.S. PATENT DOCUMENTS

| | | | |
|---|---|---|---|
| 3,862,958 A | | 1/1975 | Ruechardt et al. |
| 5,612,360 A | | 3/1997 | Boyd et al. |
| 5,621,082 A | | 4/1997 | Xiong et al. |
| 5,705,499 A | | 1/1998 | Cywin et al. |
| 5,733,920 A | | 3/1998 | Mansuri et al. |
| 5,760,028 A | | 6/1998 | Jadhav et al. |
| 5,846,990 A | | 12/1998 | Murugesan Natesan et al. |
| 5,886,195 A | | 3/1999 | Tang et al. |
| 5,916,908 A | * | 6/1999 | Giese et al. ............ 514/406 |
| 6,020,336 A | | 2/2000 | Lavielle et al. |

FOREIGN PATENT DOCUMENTS

| | | |
|---|---|---|
| DE | 273 062 | 11/1989 |
| EP | 0 666 270 | 8/1982 |
| EP | 0 369 145 | 5/1990 |
| EP | 0 816 357 | 1/1998 |
| JP | 63030563 | 2/1988 |
| WO | WO 86/05779 | 10/1986 |
| WO | WO 92/20642 | 11/1992 |
| WO | WO 93/19052 | 9/1993 |
| WO | WO 94/14780 | 7/1994 |
| WO | WO 96/14843 | 5/1996 |
| WO | WO 96/23783 | 8/1996 |
| WO | WO 97/03967 | 2/1997 |
| WO | WO 97/16447 | 5/1997 |
| WO | WO 97/34876 | 9/1997 |
| WO | WO 97/40019 | 10/1997 |
| WO | WO 97/42949 | 11/1997 |
| WO | WO 98/02162 | 1/1998 |
| WO | WO 98/03487 | 1/1998 |
| WO | WO 98/09961 | 3/1998 |
| WO | WO 98/14451 | 4/1998 |
| WO | WO 98/17662 | 4/1998 |
| WO | WO 98/33798 | 8/1998 |
| WO | WO 98/38168 | 9/1998 |
| WO | WO 99/02162 | 1/1999 |
| WO | WO 99/06280 | 2/1999 |
| WO | WO 99/06540 | 2/1999 |
| WO | WO 99/15500 | 4/1999 |
| WO | WO 99/17769 | 4/1999 |
| WO | WO 99/21845 | 5/1999 |
| WO | WO 99/23076 | 5/1999 |
| WO | WO 99/23077 | 5/1999 |
| WO | WO 99/24416 | 5/1999 |
| WO | WO 99/43663 | 9/1999 |
| WO | WO 99/43675 | 9/1999 |
| WO | WO 99/43676 | 9/1999 |
| WO | WO 99/54308 | 10/1999 |
| WO | WO 99/65884 | 12/1999 |
| WO | WO 00/18761 | 4/2000 |
| WO | WO 00/66112 | 11/2000 |

OTHER PUBLICATIONS

Al–Khodairy et al., *Molec. Biol. Cell*, 5, 147–160 (1994).
Alon, et. al, *Nat. Med.*, 1, 1024 (1995).
Bagshawe, *Drug Dev. Res.*, 34, 220–230 (1995).
Baiocchi et al., *Heterocyclic Chem.*, 16, 1469–1474 (1979).
Bandara, et al., *Nature Biotechnology*, vol. 15 (1997), pp. 896–901.
Bertolini et al., *J. Med. Chem.*, 40, 2011–2016 (1997).
Bodor, *Advances in Drug Res.*, 13, 255–331 (1984).
Bolen, *Oncogene*, 8, 2025–2031 (1993).
Braun–Dullaeus et al., *Circulation*, 98, 82–89 (1998).
Bundgaard, *Design of Prodrugs* (Elsevier Press 1985).
Bunz et al., *Science*, 282,1497–1501 (1998).
Castro et al., *J. Med Chem*, 39:842–849 (1996).
Chang, et al., *Chemistry & Biology*, vol. 6 (1999), pp. 361–375.
Chen, et al., *Proceedings of the National Academy of Science*, USA, vol. 96 (1999), pp. 4325–4329.
Cohen, et al., *Proc. Natl. Acad. Sci. U. S. A.*, vol. 95 (1998), pp. 14272–14277.
Cohen, *Curr. Op. Chem. Biol.*, 3, 459–465 (1999).
Danheiser et al., *J. Amer. Chem. Soc.*, vol. 112, pp. 3093–3100 (1990).

(List continued on next page.)

Primary Examiner—Charanjit S. Aulakh
(74) Attorney, Agent, or Firm—Shanks & Herbert

(57) ABSTRACT

Amino-pyrazole compounds that modulate and/or inhibit the activity of protein kinases. These compounds and pharmaceutical compositions containing them are capable of mediating and/or inhibiting the activity cyclin-dependent kinases, thereby modulating and/or inhibiting unwanted cell proliferation. The invention is also directed to the therapeutic or prophylactic use of pharmaceutical compositions containing such compounds, and to methods of treating cancer as well as other disease states associated with unwanted angiogenesis and/or cellular proliferation, such as diabetic retinopathy, neovascular glaucoma, rheumatoid arthritis, and psoriasis, by administering effective amounts of such compounds.

12 Claims, No Drawings

OTHER PUBLICATIONS

Folkman, *Nature Med.*, 1, 27–31 (1995).
Gray et al., *Science*, vol. 281 (1998), pp. 533–538.
Hall and Peters, *Adv. Cancer Res.*, vol. 68, pp.67–108 (1996).
Harper, *Cancer Surv.*, vol. 29, pp. 91–107(1997).
Hartwell et al., *Science*, 246, 629–634 (1989).
Hartwell et al., *Science*, 266, 1821–1828 (1994).
Holash et al., *Oncogene*, 18, 5356–62 (1999).
Kamb et al., *Science*, 264, 436–440 (1994).
Kamb, *Trends in Genetics*, 11, 136–140 (1995).
Katsura et al., *Chem Pharm Biol*, 40(8), 2062–2074–140 (1992).
Klohs et al., *Curr. Op. Chem. Biol.*, 10, 544–49 (1999).
Klunder et al., *J. Med. Chem.*; 1998, 41, 2960–2971.
Krogsgaard–Larsen et al., eds., Harwood Academic Publishers, 1991.
Lee et al., *Biochem*, 23, 4255 (1984).
Legravend et al., *Bioorg. Med. Chem. Lett.*, vol. 8(1998), pp. 793–798.
Lin et al., *J Med Chem.*, 15(6), 615 (1972).
Loda et al., *Nature Medicine*, vol. 3(1997), pp. 231–234.
Lukas et al, *Genes and Dev.*, vol. 11, pp. 1479–1492 (1997).
Lutty and McLeod, *Arch. Ophthalmol.*, 110, 267 (1992).
Maisonpierre et al., *Science*, 277, 55–60 (1997).
Matsuoka, *Science*, 282, 1893–1897 (1998).
McMahon et al, *Oncologist*, 5, 3–10 (2000).
McMahon et al., *Current Opinion in Drug Discovery & Development*, 1, 131–146 (1998).
Meijer and Kim, *Methods in Enzymol,*. vol. 283 (1997), pp. 113–128.
Merenmines et al., *Cell Growth & Differentiation*, 8, 3–10 (1997).
Millauer et al., *Cancer Research*, 56, 1615–1620 (1996).
Mohammadi et al., *EMBO Journal*, 17, 5896–5904 (1998).
Mohammadi et al., *Mol. Cell. Biol.*, 16, 977–989 (1996).
Morgan, D., *Ann. Rev. Cell Dev. Biol.*, vol. 13, pp. 261–291(1997).
Mossman, Journal of Immunological Methods, vol.65, pp. 55–58(1983).
Mylari et al., *J. Med. Chem.*, 35, 457–465 (1992).
Nasmyth, K., *Science*, 274, 1643–1677 (1996).
Nobori et al., *Nature*, vol. 368, pp. 753–775 (1994).
Nurse, *Cell*, 91, 865–867 (1997).
O'Connor, *Cancer Surveys*, 29, 151–182 (1997).
Owa, et al., *J. Med. Chem.*, vol. 42 (1999), pp. 3789–3799.
Parast C. et al., *BioChemistry*, 37, 16788–16801 (1998).
Peng et al., *Science*, 277, 1501–1505 (1997).
Penn et. al, *Invest. Ophthalmol. Vis. Sci.*, 36, 2063, (1995).
Rosenblatt et al., *J. Mol. Biol.*, 230, 1317–1319 (1993).
Rosowsky et al, *J. Med Chem.*, 31, 763–768 (1988).
Sanchez et al., *Science*, 277, 1497–1501 (1997).
Sarodnick et al, *J. Prakt. Chem.* 339, 714–720 (1997).
Schang et al., *J. Virol.* 74, 2107–2120 (2000).
Schow et al., *Bioorg. Med. Chem. Lett.*, vol. 7 (1997), pp. 2697–2702.
Schultz, et al., *J. Med. Chem.*, vol. (1999), pp. 2909–2919.
Shan, et al., *J. Pharm. Sci.*, 86(7), 765–767 (1997).
Sherr, et al., *Genes Dev.*, vol. 13 (1999), pp. 1501–1512.
Still et al., *J. Org. Chem.*, 43, 2923 (1978).
Stone, et al, *J. Neurosci.*, 15, 4738 (1995).
Strawn et al., *Cancer Research*, 56, 3540–3545 (1996).
Strawn et al., *Exp. Opin. Invest. Drugs*, 7, 553–573 (1998).
Taniguchi et al., *Nature Med.*, 5, 760–767(1999).
Thomas et al., *J. Biol. Chem.*, 274, 36684–92 (1999).
Thompson, *Oncogene*, 15, 3025–3035 (1997).
Vishwakarma et al., Indian J. Chem vol. 24B, pp. 472–476 (1985).
Walworth et al., *Nature*, 363, 368–371 (1993).
Weinert, *Science*, 277, 1450–1451 (1997).
Winters et al., *Oncogene*, 17, 673–684 (1998).
Yoshiji et al., *Cancer Research*, 57, 3924–3928 (1997).
Zeng et al., *Nature*, 395, 507–510 (1998).
Hünig et al., "Heterocyclen aus Enamin–Isothiocyanat–Addukten", *Chemische Berichte*, 95, 937–943 (1962).
Sayed et al., "Some reactions of 3–methyl–1–phenyl–4–(phenylaminothiocarbonyl)–.Delta. 2–pyrazolin–5–one", *Chemical Abstracts*, 131, No. 12, Abst. 157727 (9120/1999).
Shaefer et al., "Substituted 4–nitropyrazoles from nitroketenaminals", *Chemical Abstracts*, 95, No.13, Abst. 115376 (9/28/1981).
Takahata et al., "Activated lactams: new syntheses of azacycloalka'2,3–d!pyramidine and —'2,3–c!pyrazole derivatives", *Chemical Abstracts*, 98, No. 25, Abst. 215558 (6/20/1983).
International Search Report, PCT/US 01/10977, (4/20/2001).
Amin et al., *J. Chem. Soc. Perkin Trans.*, 2:1489–1492 (1982).
Bodor, N., *Advances in Drug Res.*, 13:256–331 (1984).
Bunz et al., *Science*, 282: 1497–1501 (1998).
DelSal et al., *Critical Rev .in Oncogenesis*, 7(1&2): 127–142 (1996).
Grant et al., *Proc. Amer. Assoc. Cancer Res.*, 39, Abst. 1207 (1998).
Greene and Wutz, Protecting Groups in Organic Synthesis, $2^{nd}$ edition, John Wiley and Sons, New York, New York, 749–779 (1991).
Jeffrey et al., *Nature*, 376:313–320 (1995).
Larsen, I. K., "Chapter 5–Design and Applications of Prodrugs", *Drug Design and Development*, Krogsgaard–Larsen et al., eds., Harwood Academic Publishers, Switzerland (1991).
Luzzio et al., *Proc. Amer. Assoc. Cancer Res.* Abst. 4102 (1999).
MacDowell, D.W.H, et al., *J. Org. Chem.*, 35(4):871–875 (1970).
McTigue et al., *Structure*, 7(3):319–330 (1999).
Meyer et al., *Proc. Amer. Assoc. Cancer Res.*, 39, Abst. 3794 (1998).
Mohammadi et al., *EMBO Journal*, 17(20):5896–5904 (1998).
Morgan, *Ann. Rev. Cell Dev. Biol.*, 13:261–291 (1997).
Munro et al., *J. Chem. Soc. Perkin. Trans.*, 1:1718–1723 (1980).
Nasmyth, *Science*, 274: 1643–1677 (1996).
Ple, P.A.; Marnett, L. J., *J. Heterocycl. Chem.*, 25: 1271–1272 (1998).
Ruetz et al., *Proc. Amer. Assoc. Cancer Res.*, 39, Abst. 3796 (1998).
Sedlacek et al., *Int. J. Oncol.*, 9: 1143–1168 (1996).
Seitz et al., $218^{th}$ ACS Natl. Mtg., Abst. MEDI 316 (Aug. 22–26, 1999, New Orleans).
Stover et al., *Curr. Opin. in Drug Discov. and Devel.*, 2(4): 274–285 (1999).
Titus, R.L.;Titus, C. F., *J. Heterocycl. Chem.*, 10: 679–681 (1973).
Webster *Exp. Opin. Invest. Drugs*, 7(6): 865–887 (1998).

\* cited by examiner ure.
COMPOUNDS, PHARMACEUTICAL COMPOSITIONS, AND METHODS FOR INHIBITING PROTEIN KINASES This application claims the benefit of U.S. Provisional Application No. 60/197,862, filed Apr. 18, 2000, which is incorporated herein by reference in its entirety.

FIELD OF THE INVENTION

This invention is directed to amino-pyrazole compounds that mediate and/or inhibit the activity of protein kinases, such as cyclin-dependent kinases (CDKs), such as CDK1, CDK2, CDK4, and CDK6; VEGF, and CHK1 and to pharmaceutical compositions containing such compounds. and compositions, and to methods of treating cancer as well as other disease states associated with unwanted angiogenesis and/or cellular proliferation, by administering effective amounts of such compounds.

BACKGROUND OF THE INVENTION

Uncontrolled cell proliferation is the insignia of cancer. Cell proliferation in response to various stimuli is manifested by a deregulation of the cell division cycle, the process by which cells multiply and divide. Tumor cells typically have damage to the genes that directly or indirectly regulate progression through the cell division cycle.

Protein kinases are a family of enzymes that catalyze phosphorylation of the hydroxyl group of specific tyrosine, serine, or threonine residues in proteins. Typically, such phosphorylation dramatically perturbs the function of the protein, and thus protein kinases are pivotal in the regulation of a wide variety of cellular processes, including metabolism, cell proliferation, cell differentiation, and cell survival. Of the many different cellular functions in which the activity of protein kinases is known to be required, some processes represent attractive targets for therapeutic intervention for certain disease states. Two examples are cell-cycle control and angiogenesis, in which protein kinases play a pivotal role; these processes are essential for the growth of solid tumors as well as for other diseases.

CDKs constitute a class of enzymes that play critical roles in regulating the transitions between different phases of the cell cycle, such as the progression from a quiescent stage in $G_1$ (the gap between mitosis and the onset of DNA replication for a new round of cell division) to S (the period of active DNA synthesis), or the progression from $G_2$ to M phase, in which active mitosis and cell-division occur. See, e.g., the articles compiled in Science, vol. 274. pp. 1643–1677 (1996); and Ann. Rev. Cell Dev. Biol., vol. 13, pp. 261–291 (1997). CDK complexes are formed through association of a regulatory cyclin subunit (e.g., cyclin A, B1, B2, D1, D2, D3, and E) and a catalytic kinase subunit (e.g., cdc2 (CDK1), CDK2, CDK4, CDK5, and CDK6). As the name implies, the CDKs display an absolute dependence on the cyclin subunit in order to phosphorylate their target substrates, and different kinase/cyclin pairs function to regulate progression through specific portions of the cell cycle.

The D cyclins are sensitive to extracellular growth signals and become activated in response to mitogens during the $G_1$ phase of the cell cycle. CDK4/cyclin D plays an important role in cell cycle progression by phosphorylating, and thereby inactivating, the retinoblastoma protein (Rb). Hypophosphorylated Rb binds to a family of transcriptional regulators, but upon hyperphosphorylation of Rb by CDK4/cyclin D, these transcription factors are released to activate genes whose products are responsible for S phase progression. Rb phosphorylation and inactivation by CDK4/cyclin D permit passage of the cell beyond the restriction point of the $G_1$ phase, whereupon sensitivity to extracellular growth or inhibitory signals is lost and the cell is committed to cell division. During late $G_1$, Rb is also phosphorylated and inactivated by CDK2/cyclin E, and recent evidence indicates that CDK2/cyclin E can also regulate progression into S phase through a parallel pathway that is independent of Rb phosphorylation (see Lukas et al., Genes and Dev., vol. 11, pp. 1479–1492 (1997)).

The progression from $G_1$ to S phase, accomplished by the action of CDK4/cyclin D and CDK2/cyclin E, is subject to a variety of growth regulatory mechanisms, both negative and positive. Growth stimuli, such as mitogens, cause increased synthesis of cyclin D1 and thus increased functional CDK4. By contrast, cell growth can be "reined in," in response to DNA damage or negative growth stimuli, by the induction of endogenous inhibitory proteins. These naturally occurring protein inhibitors include $p21^{WAF1/ClP1}$, $p27^{K1P1}$, and the $p16^{1NK4}$ family, the latter of which inhibit CDK4 exclusively (see Harper, Cancer Surv., vol. 29, pp. 91–107 (1997)). Aberrations in this control system. particularly those that affect the function of CDK4 and CDK2, are implicated in the advancement of cells to the highly proliferative state characteristic of malignancies, such as familial melanomas, esophageal carcinomas, and pancreatic cancers (see, e.g., Hall et al., Adv. Cancer Res., vol. 68, pp. 67–108 (1996); and Kamb et al., Science, vol. 264, pp. 436–440 (1994)). Over-expression of cyclin D1 is linked to esophageal, breast, and squamous cell carcinomas (see, e.g., DelSal et al., Critical Rev. Oncogenesis, vol. 71, pp. 127–142 (1996)). Genes encoding the CDK4-specific inhibitors of the p16 family frequently have deletions and mutations in familial melanoma, gliomas, leukemias, sarcomas, and pancreatic, non-small cell lung, and head and neck carcinomas (see Nobori et al., Nature, vol. 368, pp. 753–75 (1994)). Amplification and/or overexpression of cyclin E has also been observed in a wide variety of solid tumors, and elevated cyclin E levels have been correlated with poor prognosis. In addition, the cellular levels of the CDK inhibitor p27, which acts as both a substrate and inhibitor of CDK2/cyclin E, are abnormally low in breast, colon, and prostate cancers, and the expression levels of p27 are inversely correlated with the stage of disease (see Loda et al., Nature Medicine, vol. 3, pp. 231–234 (1997)). Recently there is evidence that CDK4/cyclin D might sequester p27, as reviewed in Sherr, et al., Genes Dev., vol. 13, pp. 1501–1512 (1999). The p21 proteins also appear to transmit the p53 tumor-suppression signal to the CDKs; thus, the mutation of p53 in approximately 50% of all human cancers may indirectly result in deregulation of CDK activity.

The emerging data provide strong validation for the use of compounds inhibiting CDKs, and CDK4 and CDK2 in particular, as anti-proliferative therapeutic agents. Certain biomolecules have been proposed for this purpose. For example, U.S. Pat. No. 5,621,082 to Xiong et al. discloses nucleic acid encoding of inhibitors of CDK6; WIPO Publication No. WO 99/06540 discloses nucleic acids encoding for inhibitors of CDK's. Peptides and peptidomimetic inhibitors are described in European Patent Publication No. 0 666 270 A2, Bandara et al., Nature Biotechnology, vol. 15, pp. 896–901 (1997) and Chen, et al., Proc. Natl. Acad. Sci. U. S. A, vol. 96, pp. 4325–4329 (1999). Peptide aptamers were identified from screening in Cohen, et al., Proc. Natl. Acad. Sci. U. S. A., vol. 95, pp. 14272–14277 (1998). Several small molecules have been identified as CDK inhibitors (for recent reviews, see Webster, Exp. Opin. Invest.

Drugs, vol. 7, pp. 865–887 (1998), and Stover, et al., *Curr. Opin. in Drug Discov. and Devel.*, vol. 2, pp. 274–285 (1999)). The flavone flavopiridol displays modest selectivity for inhibition of CDKs over other kinases, but inhibits CDK4, CDK2, and CDK1 equipotently, with $IC_{50}$s in the 0.1–0.3 μM range. Flavopiridol is currently in Phase II clinical trials as an oncology chemotherapeutic (Sedlacek et al., *Int. J. Oncol.*, vol. 9, pp. 1143–1168 (1996)). Analogs of flavopiridol are the subject of other publications, for example, U.S. Pat. No. 5,733,920 to Mansuri et al. (WIPO Publication No. WO 97/16447) and WIPO Publication Nos. WO 97/42949 and WO 98/17662. Results with purine-based derivatives are described in Schow et al., *Bioorg. Med. Chem. Lett.*, vol. 7, pp. 2697–2702 (1997); Grant et al., *Proc. Amer. Assoc. Cancer Res,.* vol. 39, Abst. 1207 (1998); Legravend et al., *Bioorg. Med. Chem. Lett.*, vol. 8, pp. 793–798 (1998); Gray et al., *Science*, vol. 281, pp. 533–538 (1998); Chang, et al., *Chemistry & Biology*, vol. 6, pp. 361–375 (1999); and WIPO Publication Nos. WO 99/02162, WO 99/43675, and WO 99/43676. In addition, the following publications disclose certain pyrimidines that inhibit cyclin-dependent kinases and growth-factor mediated kinases: WIPO Publication No. WO 98/33798; Ruetz et al., *Proc. Amer. Assoc. Cancer Res,.* vol. 39, Abst. 3796 (1998); and Meyer et al., *Proc. Amer. Assoc. Cancer Res.*, vol. 39, Abst. 3794 (1998).

Benzensulfonamides that block cells in G1 are in development by Eisai Inc. (Teaneck, N.J.). See, for example, Owa. et al., *J. Med. Chem.*, vol. 42, pp. 3789–3799 (1999). An oxindole CDK inhibitor is in development by Glaxo-Wellcome, see Luzzio, et al., *Proc. Amer. Assoc. Cancer Res.*, vol., Abst. 4102 (1999) and WIPO Publication No. WO 99/15500. Paullones were found in collaboration with the National Cancer Institute, Schultz, et al., *J. Med. Chem.*, vol. 42(15), pp. 2909–2919 (1999). Indenopyrazoles are described in WIPO Publication No. WO 99/17769 and by Seitz, et al, $218^{th}$ ACS Natl. Mtg, Abst MEDI 316 (Aug. 22–26, 1999, New Orleans). Aminothiazoles are described in WIPO Publication Nos. WO 99/24416 and WO 99/21845. Isothiazole derivatives are described in WIPO Publication No. WO 99/6280. Pyrazole inhibitors of protein kinases are described in WIPO Publication No. WO 96/14843. Pyrazole-4-one analogs are described in WIPO Publication No. WO 99/54308. 5-Aminopyrazoles as inhibitors of protein tyrosine kinase p56lck are described in WIPO Publication No. WO 97/40019.

CHK1 is another protein kinase. CHK1 plays an important role as a checkpoint in cell cycle progression. Checkpoints are control systems that coordinate cell cycle progression by influencing the formation, activation and subsequent inactivation of the cyclin-dependent kinases. Checkpoints prevent cell cycle progression at inappropriate times, maintain the metabolic balance of cells while the cell is arrested, and in some instances can induce apoptosis (programmed cell death) when the requirements of the checkpoint have not been met. See, e.g., O'Connor, *Cancer Surveys*, vol. 29, pp. 151–182 (1997); Nurse, *Cell*, vol. 91, pp. 865–867 (1997); Hartwell et al., *Science*, vol. 266, pp. 1821–1828 (1994); Hartwell et al., *Science*, vol. 246, pp. 629–634 (1989).

One series of checkpoints monitors the integrity of the genome and, upon sensing DNA damage, these "DNA damage checkpoints" block cell cycle progression in $G_1$ & $G_2$ phases, and slow progression through S phase. O'Connor, *Cancer Surveys*, vol. 29, pp. 151–182 (1997); Hartwell et al., *Science*, vol. 266, pp. 1821–1828 (1994). This action enables DNA repair processes to complete their tasks before replication of the genome and subsequent separation of this genetic material into new daughter cells takes place. Importantly, the most commonly mutated gene in human cancer, the p53 tumor suppressor gene, produces a DNA damage checkpoint protein that blocks cell cycle progression in $G_1$ phase and/or induces apoptosis (programmed cell death) following DNA damage. Hartwell et al., *Science*, vol. 266, pp. 1821–1828 (1994). The p53 tumor suppressor has also been shown to strengthen the action of a DNA damage checkpoint in $G_2$ phase of the cell cycle. See, e.g., Bunz et al., *Science*, vol. 28, pp. 1497–1501 (1998); Winters et al., *Oncogene*, vol. 17, pp. 673–684 (1998); Thompson, *Oncogene*, vol. 15, pp. 3025–3035 (1997).

Given the pivotal nature of the p53 tumor suppressor pathway in human cancer, therapeutic interventions that exploit vulnerabilities in p53-defective cancer have been actively sought. One emerging vulnerability lies in the operation of the $G_2$ checkpoint in p53 defective cancer cells. Cancer cells, because they lack $G_1$ checkpoint control, are particularly vulnerable to abrogation of the last remaining barrier protecting them from the cancer killing effects of DNA-damaging agents: the $G_2$ checkpoint. The $G_2$ checkpoint is regulated by a control system that has been conserved from yeast to humans. Important in this conserved system is a kinase, CHK1, which transduces signals from the DNA-damage sensory complex to inhibit activation of the cyclin B/Cdc2 kinase, which promotes mitotic entry. See, e.g., Peng et al., *Science*, vol. 277, pp. 1501–1505 (1997); Sanchez et al., *Science*, vol. 277, pp. 1497–1501 (1997). Inactivation of CHK1 has been shown to both abrogate $G_2$ arrest induced by DNA damage inflicted by either anticancer agents or endogenous DNA damage, as well as result in preferential killing of the resulting checkpoint defective cells. See, e.g., Nurse, *Cell*, vol. 91, pp. 865–867 (1997); Weinert, *Science*, vol. 277, pp. 1450–1451 (1997); Walworth et al., *Nature*, vol. 363, pp. 368–371 (1993); and Al-Khodairy et al., *Molec. Biol. Cell*, vol. 5, pp. 147–160 (1994).

Selective manipulation of checkpoint control in cancer cells could afford broad utilization in cancer chemotherapeutic and radiotherapy regimens and may, in addition, offer a common hallmark of human cancer "genomic instability" to be exploited as the selective basis for the destruction of cancer cells. A number of factors place CHK1 as a pivotal target in DNA-damage checkpoint control. The elucidation of inhibitors of this and functionally related kinases such as CDS1/CHK2, a kinase recently discovered to cooperate with CHK1 in regulating S phase progression (see Zeng et al., *Nature*, vol. 395, pp. 507–510 (1998); Matsuoka, *Science*, vol. 282, pp. 1893–1897 (1998)), could provide valuable new therapeutic entities for the treatment of cancer.

Another group of kinases are the tyrosine kinases. Tyrosine kinases can be of the receptor type (having extracellular, transmembrane and intracellular domains) or the non-receptor type (being wholly intracellular). At least one of the non-receptor protein tyrosine kinases, namely, LCK, is believed to mediate the transduction in T-cells of a signal from the interaction of a cell-surface protein (Cd4) with a cross-linked anti-Cd4 antibody. A more detailed discussion of non-receptor tyrosine kinases is provided in Bolen, *Oncogene*, vol. 8, pp. 2025–2031 (1993), which is incorporated herein by reference.

In addition to its role in cell-cycle control, protein kinases also play a crucial role in angiogenesis, which is the mechanism by which new capillaries are formed from existing vessels. When required, the vascular system has the potential to generate new capillary networks in order to maintain the proper functioning of tissues and organs. In the adult, however, angiogenesis is fairly limited, occurring only in the process of wound healing and neovascularization of the endometrium during menstruation. See Merenmies, J., Parada, L. F., Henkemeyer, M., *Cell Growth & Differentiation*, vol. 8, pp. 3–10 (1997). On the other hand, unwanted angiogenesis is a hallmark of several diseases, such as retinopathies, psoriasis, rheumatoid arthritis, age-related macular degeneneration, and cancer (solid tumors). Folkman, *Nature Med.*, vol. 1, pp. 27–31 (1995). Protein kinases which have been shown to be involved in the angiogenic process include three members of the growth factor receptor tyrosine kinase family: VEGF-R2 (vascular endothelial growth factor receptor 2, also know as KDR (kinase insert domain receptor) and as FLK-1); FGF-R (fibroblast growth factor receptor); and TEK (also known as Tie-2).

VEGF-R2, which is expressed only on endothelial cells, binds the potent angiogenic growth factor VEGF and mediates the subsequent signal transduction through activation of its intracellular kinase activity. Thus, it is expected that direct inhibition of the kinase activity of VEGF-R2 will result in the reduction of angiogenesis even in the presence of exogenous VEGF (see Strawn et al., *Cancer Research*, vol. 56, pp. 3540–3545 (1996)), as has been shown with mutants of VEGF-R2 which fail to mediate signal transduction. Millauer et al., *Cancer Research*, vol. 56, pp. 1615–1620 (1996). Furthermore, VEGF-R2 appears to have no function in the adult beyond that of mediating the angiogenic activity of VEGF. Therefore, a selective inhibitor of the kinase activity of VEGF-R2 would be expected to exhibit little toxicity.

Similarly, FGF-R binds the angiogenic growth factors aFGF and bFGF and mediates subsequent intracellular signal transduction. Recently, it has been suggested that growth factors such as bFGF may play a critical role in inducing angiogenesis in solid tumors that have reached a certain size. Yoshiji et al., *Cancer Research*, vol. 57, pp. 3924–3928 (1997). Unlike VEGF-R2, however, FGF-R is expressed in a number of different cell types throughout the body and may or may not play important roles in other normal physiological processes in the adult. Nonetheless, systemic administration of a small molecule inhibitor of the kinase activity of FGF-R has been reported to block bFGF-induced angiogenesis in mice without apparent toxicity. Mohammad et al., *EMBO Journal*, vol. 17, pp. 5996–5904 (1998).

TEK (also known as Tie-2) is another receptor tyrosine kinase expressed only on endothelial cells which has been shown to play a role in angiogenesis. The binding of the factor angiopoietin-1 results in autophosphorylation of the kinase domain of TEK and results in a signal transduction process which appears to mediate the interaction of endothelial cells with peri-endothelial support cells, thereby facilitating the maturation of newly formed blood vessels. The factor angiopoietin-2, on the other hand, appears to antagonize the action of angiopoietin-1 on TEK and disrupts angiogenesis. Maisonpierre et al., *Science*, vol. 277, pp. 55–60 (1997).

As a result of the above-described developments, it has been proposed to treat angiogenesis by the use of compounds inhibiting the kinase activity of VEGF-R2, FGF-R, and/or TEK. For example, WIPO Publication No. WO 97/34876 discloses certain cinnoline derivatives that are inhibitors of VEGF-R2, which may be used for the treatment of disease states associated with abnormal angiogenesis and/or increased vascular permeability such as cancer, diabetes, psoriasis, rheumatoid arthritis, Kaposi's sarcoma, haemangioma, acute and chronic nephropathies, atheroma, arterial restinosis, autoimmune diseases, acute inflammation and ocular diseases with retinal vessel proliferation.

In addition to the protein kinases identified above, many other protein kinases have been considered to be therapeutic targets, and numerous publications disclose inhibitors of kinase activity, as reviewed in the following: McMahon et al., *Current Opinion in Drug Discovery & Development*. vol. 1, pp. 131–146 (1998); Strawn et al., *Exp. Opin. Invest. Drugs*, vol. 7, pp. 553–573 (1998).

There is still a need, however, for other small-molecule compounds that may be readily synthesized and are potent inhibitors of one or more protein kinases, such as CHK1, VEGF, and CDKs or CDK/cyclin complexes. Because CDK4 may serve as a general activator of cell division in most cells, and because complexes of CDK4/cyclin D and CDK2/cyclin E govern the early $G_1$ phase of the cell cycle, there is a need for effective and specific inhibitors of CDK4 and/or CDK2 for treating one or more types of tumors.

SUMMARY OF THE INVENTION

Accordingly, one object of the invention is to attain compounds and drug compositions that inhibit the activity of one or more protein kinases, such as VEGF, CHK1 and/or CDKs, such as CDK2, CDK4, and/or CDK6, or cyclin complexes thereof. Such compounds and compositions may be used to inhibit mammalian kinases/cyclin kinases, insect kinases, and fungal kinases.

A further object is to provide an effective method of treating cancer indications through kinase inhibition, such as through inhibition of CDK4 or CDK4/D-type cyclin complexes and/or CDK2 or CDK2/E-type cyclin complexes. Another object is to achieve pharmaceutical compositions containing compounds effective to block the transition of cancer cells into their proliferative phase. These and other objects and advantages of the invention, which will become apparent in light of the detailed description below, are achieved through use of cell-cycle control agents of the invention described below.

According to one general aspect, the invention is directed to compounds of the Formula I

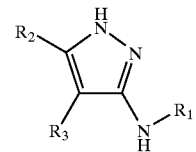

Formula I wherein:
 $R_1$ is a substituted or unsubstituted alkyl, aryl, heteroaryl, cycloalkyl, or heterocycloalkyl,
 $R_2$ is a substituted or unsubstituted heteroaryl or heterocycloalkyl, and
 $R_3$ is hydrogen, halogen, (fluorine, chlorine, bromine, or iodine) or a substituted or unsubstituted $C_{1-8}$ alkyl, or
 $R_2$ and $R_3$ together form a substituted or unsubstituted 5-membered aryl, heteroaryl, cycloalkyl, or heterocycloalkyl.

The invention is also directed to pharmaceutically acceptable salts of compounds of the Formula I. The invention is further directed to pharmaceutically acceptable prodrugs of compounds of the Formula I. Additionally, the invention is directed to pharmaceutically active metabolites of compounds of the Formula I, and to pharmaceutically acceptable salts of such metabolites.

In another general aspect, the invention is directed to a pharmaceutical compositions, each comprising:
(a) a cell-cycle control agent selected from a compound of the Formula I, a pharmaceutically acceptable salt of a compound of the Formula I, a pharmaceutically acceptable prodrug of a compound of the Formula I, a pharmaceutically active metabolite of compound of the Formula I, and a pharmaceutically acceptable salt of such a metabolite; and
(b) a pharmaceutically acceptable carrier.

There is further provided in accordance with another general aspect of the invention, a method of using the compounds of Formula I as cell-cycle control agents for treating diseases or disorders mediated by protein kinases inhibition. such as those mediated by CDK4 and/or CDK2 inhibition by administering to a patient in need thereof, a compound of Formula I, a pharmaceutically acceptable salt of a compound of the Formula I, a pharmaceutically acceptable prodrug of a compound of the Formula I, a pharmaceutically active metabolite of a compound of the Formula I, or pharmaceutically acceptable salt of such a metabolite of a compound of the Formula I.

The invention further provides a method of treating malignancies, comprising administering effective amounts of a compound of Formula I, a pharmaceutically acceptable salt of a compound of the Formula I, a pharmaceutically acceptable prodrug of a compound of the Formula I, a pharmaceutically active metabolite of a compound of the Formula I, or pharmaceutically acceptable salt of such a metabolite of a compound of the Formula I.

The invention further provides a method of treating cancer, comprising administering effective amounts of a compound of Formula I, a pharmaceutically acceptable salt of a compound of the Formula I, a pharmaceutically acceptable prodrug of a compound of the Formula I, a pharmaceutically active metabolite of a compound of the Formula I, or pharmaceutically acceptable salt of such a metabolite of a compound of the Formula I.

The invention further provides a method of treating a disease state associated with unwanted angiogenesis and/or cellular proliferation, comprising administering effective amounts of a compound of Formula I, a pharmaceutically acceptable salt of a compound of the Formula I, a pharmaceutically acceptable prodrug of a compound of the Formula I, a pharmaceutically active metabolite of a compound of the Formula I, or pharmaceutically acceptable salt of such a metabolite of a compound of the Formula I.

The invention further provides a method of treating mycotic infection, comprising administering effective amounts of a compound of Formula I, a pharmaceutically acceptable salt of a compound of the Formula I, a pharmaceutically acceptable prodrug of a compound of the Formula I, a pharmaceutically active metabolite of a compound of the Formula I, or pharmaceutically acceptable salt of such a metabolite of a compound of the Formula I.

The invention also provides a method of modulating and/or inhibiting the kinase activity of a protein kinase complex by administering a compound of the Formula I, a pharmaceutically acceptable salt of a compound of the Formula I, a pharmaceutically acceptable prodrug of a compound of the Formula I, a pharmaceutically active metabolite of a compound of the Formula I, or pharmaceutically acceptable salt of such a metabolite of a compound of the Formula I to a patient in need thereof.

There is also provided in accordance with the invention, the therapeutic use of a pharmaceutical composition containing a compound of the Formula I, a pharmaceutically acceptable salt of a compound of the Formula I, a pharmaceutically acceptable prodrug of a compound of the Formula I, a pharmaceutically active metabolite of a compound of the Formula I, or pharmaceutically acceptable salt of such a metabolite of a compound, to control proliferation, differentiation and/or apoptosis by administering There is also provided in accordance with the invention, the therapeutic use of a pharmaceutical composition containing a compound of the Formula I, a pharmaceutically acceptable salt of a compound of the Formula I, a pharmaceutically acceptable prodrug of a compound of the Formula I, a pharmaceutically active metabolite of a compound of the Formula I, or pharmaceutically acceptable salt of such a metabolite of a compound, in treating diseases mediated by kinase activity, such as cancer, as well as other disease states associated with unwanted angiogenesis and/or cellular proliferation, such as diabetic retinopathy, neovascular glaucoma, rheumatoid arthritis, and psoriasis.

Other aspects, advantages, and features of the invention will become apparent from the detailed description below.

DETAILED DESCRIPTION AND PREFERRED EMBODIMENTS OF THE INVENTION

The inventive compounds of the Formula I above are useful for mediating and/or inhibiting the activity of protein kinases, for example, CHK1, VEGF, and CDK/cyclin complexes, such as those active in the $G_0$ or $G_1$ stage of the cell cycle (e.g., CDK2, CDK4, and/or CDK6 complexes). The compounds of the present invention, are useful as inhibitors of mammalian kinase/cyclin complexes, insect kinase, or fungal kinase complexes. More particularly, the compounds are useful as cell-cycle control agents useful for controlling proliferation, differentiation, and/or apoptosis, thus providing treatments for cancer or other diseases associated with cellular proliferation mediated by protein kinases.

The term "alkyl" as used herein includes straight- and branched-chain alkyls having one to twelve carbon atoms. Any suitable alkyl can be used as $R_1$. Exemplary alkyls include methyl, ethyl, n-propyl, isopropyl, butyl, isobutyl, sec-butyl, tert-butyl, pentyl, isopentyl, tert-pentyl, hexyl, isohexyl, and the like. The alkyl can be substituted or unsubstituted. Suitable'substituted alkyls include fluoromethyl, difluoromethyl, trifluoromethyl, 2-fluoroethyl, 3-fluoropropyl, hydroxymethyl, 2-hydroxyethyl, 3-hydroxypropyl, and the like. The term "lower alkyl" designates an alkyl having one to eight carbon atoms (e.g., a $C_{1-8}$ alkyl). Any suitable alkyl can be used as $R_3$.

The term "alkoxy" as used herein includes the radical —O-alkyl. Illustrative examples include methoxy, ethoxy, propoxy, and the like.

The term "halogen" as used herein includes chlorine, fluorine, iodine, or bromine. The term "halo" represents chloro, fluoro, iodo, or bromo.

The term "carboxyamide" as used herein includes the radical —(C=O)—NH$_2$. The amide group (NH$_2$) can be substituted or unsubstituted.

The term "cycloalkyl" includes saturated carbocycles having from three to twelve carbon atoms, including bicyclic and tricyclic cycloalkyl structures. Suitable cycloalkyls include cyclopropyl, cyclobutyl, cyclopentyl, cyclohexyl, cycloheptyl, and the like.

The term "heterocycloalkyl" includes monocyclic radicals containing carbon atoms, preferably 4 or 5 ring carbon atoms, and at least one heteroatom selected from nitrogen, oxygen and sulfur, and having no unsaturation. Exemplary heterocycloalkyls include pyrrolidinyl, piperidinyl, thiazine and morpholinyl.

The terms "aryl" (Ar) and "heteroaryl" as used herein include monocyclic and polycyclic unsaturated aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzothiophenyl (thianaphthenyl), furanyl, thiophenyl, imidazolyl, oxazolyl, isoxazolyl, thiazolyl, triazolyl, tetrazolyl, isoquinolinyl, acridinyl, pyrimidinyl, benzimidazolyl, benzofuranyl, and the like. Any suitable fused or non-fused, monocyclic or polycyclic aryl, heteroaryl, cycloalkyl, or heterocycloalkyl can be used as $R_1$. Any suitable fused or non-fused, monocyclic or polycyclic heteroaryl or heterocycloalkyl can be used as $R_2$. Any suitable 5-membered aryl, heteroaryl, cycloalkyl or heterocycloalkyl can be formed from $R_2$ and $R_3$.

The $R_1$, $R_2$, and $R_3$ groups can be unsubstituted or substituted with any suitable substituent. Examples of suitable substituents are those found in the exemplary compounds that follows, as well as: halogen (chloro, iodo, bromo, or fluoro); $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; thiocarbonyl; sulfonyl; sulfonamide; ketone; aldehyde; ester; oxygen (=O); haloalkyl (e.g., trifluoromethyl); a cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); cycloalkyl or heterocycloalkyl, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl, S-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O. These substituents may optionally be further substituted with a substituent selected from such groups.

In a preferred embodiment, $R_1$ is substituted or unsubstituted phenyl. Preferred substituents include hydroxyl and alkoxy groups, and electron withdrawing groups such as $SO_2NH_2$ and optionally substituted carboxamides.

In a preferred embodiment, $R_2$ is a substituted or unsubstituted heteroaryl group. Especially preferred $R_2$ groups are found in the compounds of the examples, such as pyridine, thiophene, benzothiophene, indole, or benzimidazole. Especially preferred substituents for the $R_2$ group include chlorine, bromine, fluorine, hydroxy, trifluoromethyl. alkyl, S-alkyl, O-aryl, alkoxy groups, —S-aryl, and cycloalkyl groups, and the substituents in the exemplary compounds that follow.

In one preferred embodiment, $R_3$ is hydrogen. In another preferred embodiment, $R_2$ and $R_3$ form a five-membered carbocyclic ring.

In preferred embodiments, $R_1$ and $R_2$ are independently selected from the groups shown below:

$R_1$:

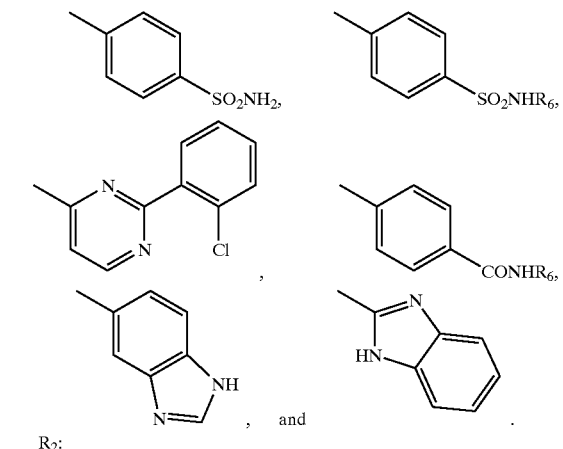

$R_2$:

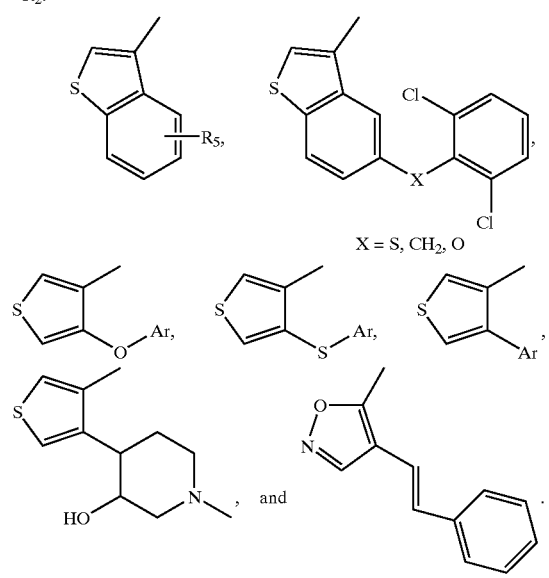

wherein:

Ar is aryl;

$R_5$ is hydrogen, $R_7$, $OR_7$, $NR_7R_7$, thioalkyl, or thioaryl; and $R_6$ is hydrogen or $R_7$; and $R_7$ is a substituted or unsubstituted alkyl, aryl, heteroaryl, cycloalkyl, or heterocycloalkyl.

Preferred compounds of the invention include:

Compound A

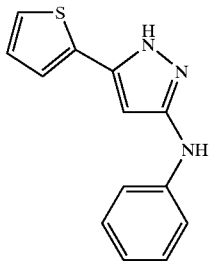

-continued
Compound B
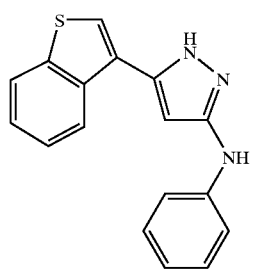
Compound C
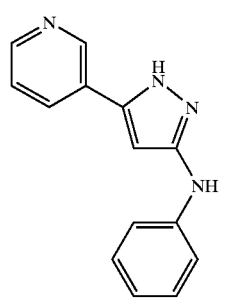
Compound D
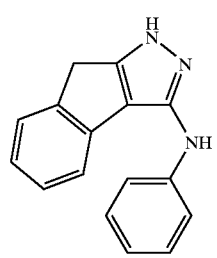
Compound E
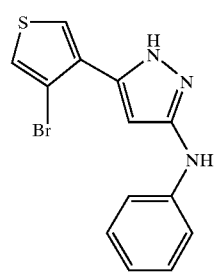
Compound F
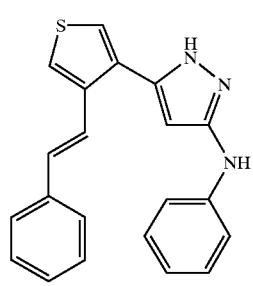
Compound G
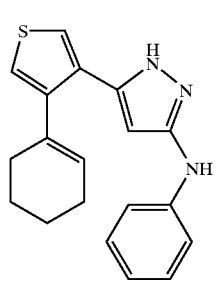
-continued
Compound H
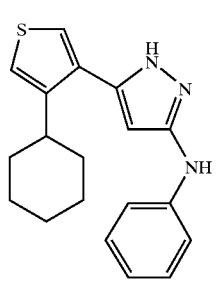
Compound I
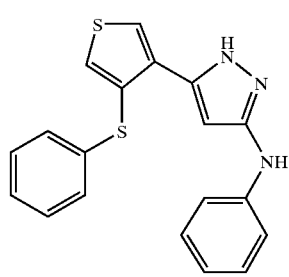
Compound J
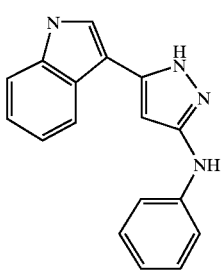
Compound K
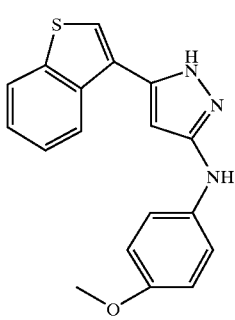
Compound L
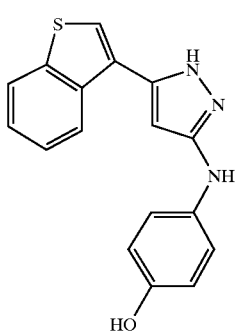

Compound M
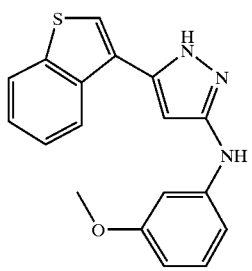
Compound N
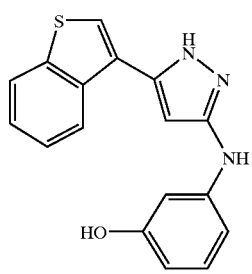
Compound O
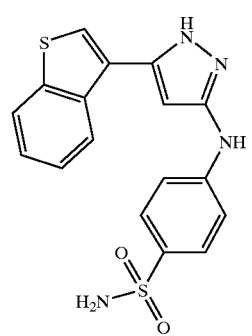
Compound P
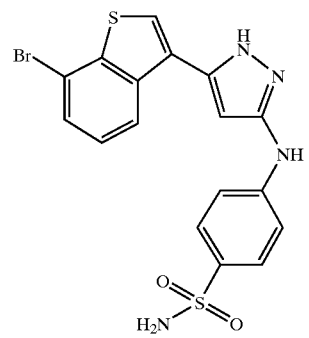
Compound Q
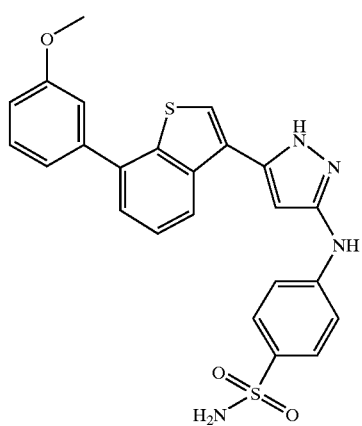
Compound R
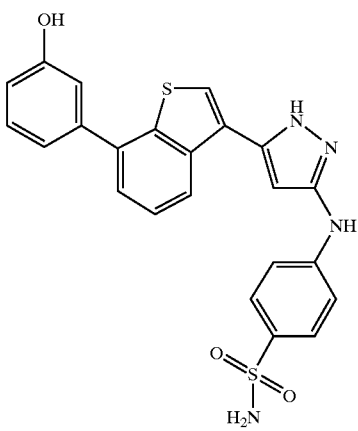
Compound S
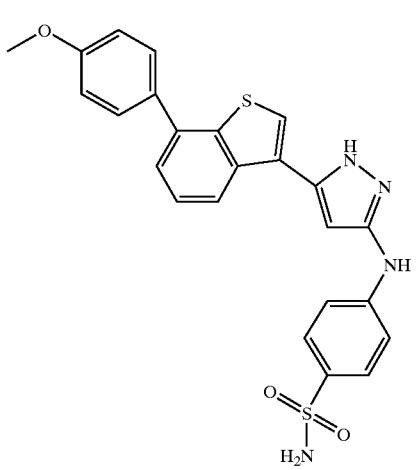
Compound T
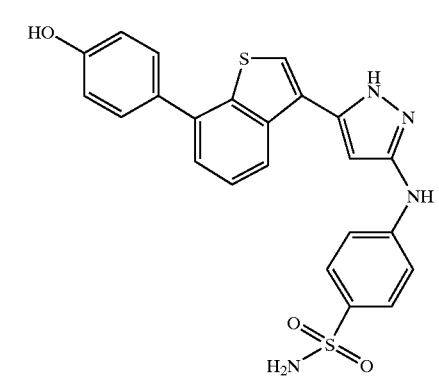
Compound U
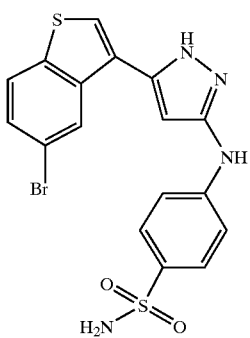

Compound V

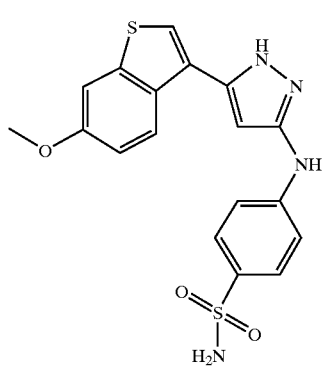

Compound W

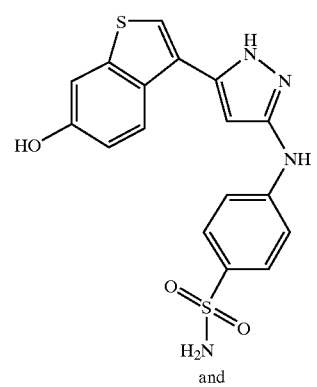

and

Compound X

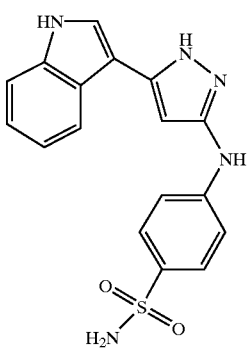

It is understood that while a compound of Formula I may exhibit the phenomenon of tautomerism, the formula drawings within this specification expressly depict only one of the possible tautomeric forms. It is therefore to be understood that the formulae are intended to represent any tautomeric form of the depicted compound and is not to be limited merely to a specific tautomeric form depicted by the formula drawings.

It is also understood that some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the. formulas are intended to cover solvated as sell as unsolvated forms of the identified structures. For example, Formula I includes compounds of the indicated structure in both hydrated and non-hydrated forms. Other examples of solvates include the structures in combination with isopropanol, ethanol, methanol, DMSO, ethyl acetate, acetic acid, or ethanolamine.

Compounds of the invention include compounds of Formula I as well as pharmaceutically acceptable salts of such compounds, pharmaceutically acceptable prodrugs of such compounds, pharmaceutically active metabolites of such compounds and pharmaceutically acceptable salts of such a metabolites.

A "pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfates, phosphates, monohydrogenphosphates, dihydrogenphosphates, metaphosphates. pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

The term "pharmaceutically acceptable prodrug" as used herein refers to a pharmaceutically acceptable compound that may be converted under physiologic conditions or by solvolysis to the specified compound or to a pharmaceutically acceptable salt of such compound. The term "pharmaceutically acceptable active metabolite" as used herein refers to a pharmacologically active product produced through metabolism in the body of a specified compound or salt thereof. Prodrugs and active metabolites of a compound may be identified using routine techniques known in the art. See, for example, Bertolini, G. et al., *J. Med.Chem.,* vol. 40, pp. 2011–2016 (1997); Shan, D. et al., *J. Pharm. Sci.,* vol. 86 (7), pp. 765–767; Bagshawe K., *Drug Dev. Res.,* vol. 34, pp. 220–230 (1995); Bodor,N., *Advances in Drug Res.,* vol. 13, pp. 224–331(1984); Bundgaard, H., ed., *Design of Prodrugs,* Elsevier Press, New York, N.Y. (1985), Larsen, I. K., "*Chapter 5—Design and Application of Prodrugs*", *Drug Design and Development,* Krogsgaard-Larsen et al., eds., Harwood Academic Publishers, Switzerland (1991). The activities of prodrugs, metabolites, and pharmaceutical salts of metabolites of compounds of the Formula I may be determined using tests such as those described herein.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrovic acid, oxalic acid, glycolic acid, salicylic acid, a pyranosidyl acid, such as glucuronic acid or galacturonic acid, an alphahydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

Pharmaceutical compositions according to the invention may, alternatively or in addition to a compound of the Formula I, comprise as an active ingredient a pharmaceutically acceptable salt of a compound of the Formula I, a prodrug of a compound of the Formula I, a pharmaceutically active metabolite of a compound of the Formula I or a pharmaceutically acceptable salt of such a metabolite. Such compounds, salts, prodrugs, and metabolites are sometimes referred to herein collectively as "cell-cycle control agents."

Cell-cycle control agents in accordance with the invention are useful as pharmaceuticals for treating proliferative disorders in mammals, especially humans, marked by unwanted proliferation of endogenous tissue. Compounds of the Formula I may be used for treating subjects having a disorder associated with excessive cell proliferation, e.g., cancers, psoriasis, immunological disorders involving undesired proliferation of leukocytes, and restenosis and other smooth-muscle disorders. Furthermore, such compounds may be used to prevent de-differentiation of post-mitotic tissue and/or cells.

Pharmaceutical compositions or preparations of the invention comprise a pharmaceutically acceptable carrier and an effective amount of at least one cell-cycle control agent. The specific dosage amount of a cell-cycle control agent being administered to obtain therapeutic or inhibitory effects may be determined in a manner known in the art according to the particular circumstances surrounding the case, including, e.g., the specific agent being administered, the route of administration, the condition being treated, and the subject or host being treated. An exemplary total daily dose of a cell-cycle control agent, which may be administered in single or multiple doses, contains a dosage level of from about 0.01 mg/kg body weight to about 50 mg/kg body weight.

The cell-cycle control agents of the invention may be administered by any of a variety of suitable routes, such as orally, rectally, transdermally, subcutaneously, intravenously, intramuscularly, or intranasally. The cell-cycle control agents are preferably formulated into compositions suitable for the desired routes before being administered.

A pharmaceutical composition or preparation according to the invention comprises an effective amount of a cell-cycle control agent and a pharmaceutically acceptable carrier, such as a diluent or excipient for the agent. When the carrier serves as a diluent, it may be a solid, semi-solid, or liquid material acting as a vehicle, excipient, or medium for the active ingredient(s). Compositions according to the invention may be made by admixing the active ingredient(s) with a carrier, or diluting it with a carrier, or enclosing or encapsulating it within a carrier, which may be in the form of a capsule, sachet, paper container, or the like. Exemplary ingredients, in addition to one or more cell-cycle control agents and any other active ingredients, include Avicel (microcrystalline cellulose), starch, lactose, calcium sulfate dihydrate, terra alba, sucrose, talc, gelatin, agar, pectin, acacia, magnesium stearate, stearic acid, peanut oil, olive oil, glyceryl monostearate, Tween 80 (polysorbate 80), 1,3-butanediol, cocoa butter, beeswax, polyethylene glycol, propylene glycol, sorbitan monostearate, polysorbate 60, 2-octyldodecanol, benzyl alcohol, glycine, sorbic acid, potassium sorbate, disodium hydrogen phosphate, sodium chloride, and water.

The compositions may be prepared in any of a variety of forms suitable for the desired mode of administration. For example, pharmaceutical compositions may be prepared in the form of tablets, pills, powders, lozenges, sachets, cachets, elixirs, suspensions, emulsions, solutions, syrups, aerosols (as solids or in liquid media), ointments (e.g., containing up to 10% by weight of a cell-cycle control agent), soft-gel and hard-gel capsules, suppositories, sterile injectable solutions, sterile packaged powders, and the like.

Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation can be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, gylcerin and the like in concentrations ranging from 0–60% of the total volume. For example, a compound of Formula I can be dissolved in DMSO and diluted with water. The composition may also be in the form of a solution of a salt form of the active ingredient in an appropriate aqueous vehicle such as water or isotonic saline or dextrose solution.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing.

Pharmaceutical compositions may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

For administration to the eye, a compound of formula I is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and selera. The pharmaceutically acceptable ophthalmic vehicle may be an ointment, vegetable oil, or an encapsulating material. A compound of the invention may also be injected directly into the vitreous and aqueous humor.

Alternatively, the active ingredient may be in powder form for constitution with a suitable vehicle, e.g., sterile pyrogen-free water, before use. The compounds may also be formulated in rectal compositions such as suppositories or retention enemas, e.g, containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids. including hydrochloric, sulfuric, acetic. lactic, tartaric, malic, succinic, etc. Salts tend to be more soluble in aqueous or other protonic solvents than are the corresponding free-base forms.

A pharmaceutical composition according to the invention comprises a cell-cycle control agent and, optionally, one or more other active ingredients, such as a known antiproliferative agent that is compatible with the cell-cycle control agent and suitable for the indication being treated.

The compounds are useful as anti-angiogenesis agents and as agents for modulating and/or inhibiting the activity of protein kinases, thus providing treatments for cancer or other diseases associated with cellular proliferation mediated by protein kinases.

Therapeutically effective amounts of the agents of the invention may be used to treat diseases mediated by modulation or regulation of protein kinases. An "effective amount" is intended to mean that amount of an agent that, when administered to a mammal in need of such treatment, is sufficient to effect treatment for a disease mediated by the activity of one or more protein kinases. Thus, e.g., a therapeutically effective amount of a compound of the Formula I, salt, active metabolite or prodrug thereof is a quantity sufficient to modulate, regulate, or inhibit the activity of one or more kinases such that a disease condition which is mediated by that activity is reduced or alleviated.

The amount of a given agent that will correspond to such an amount will vary depending upon factors such as the particular compound, disease condition and its severity, the identity (e.g., weight) of the mammal in need of treatment, but can nevertheless be routinely determined by one skilled in the art. "Treating" is intended to mean at least the mitigation of a disease condition in a mammal, such as a human, that is affected, at least in part, by the activity of one or more protein kinases, and includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

The inventive agents may be prepared using the reaction routes and synthesis schemes as described herein, employing the techniques available in the art and using starting materials that are readily available. The preparation of preferred compounds of the present invention is described in detail in the following examples, but the artisan will recognize that the chemical reactions described may be readily adapted to prepare a number of other protein kinase inhibitors of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having applicability for preparing other compounds of the invention.

Exemplary reaction routes and synthesis schemes for use in preparing the inventive agents are set forth below.

General Reaction Scheme 1

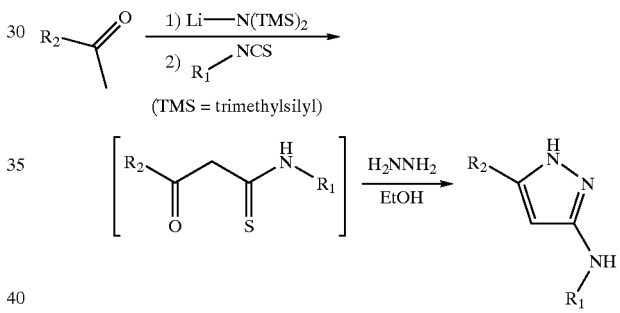

General Reaction Scheme 2

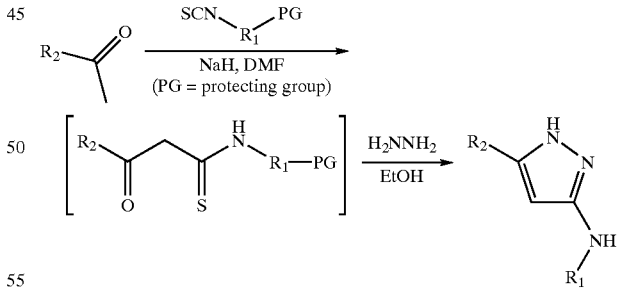

General Reaction Scheme 3

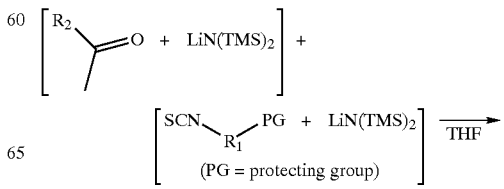

-continued

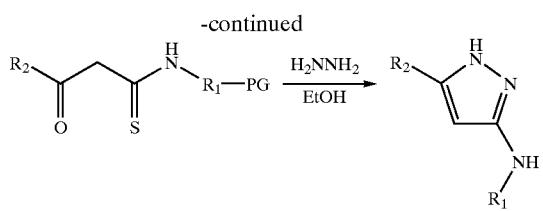

"Protecting groups" refer to groups that protect one or more inherent functional groups from premature reaction. Suitable protecting groups may be routinely selected by those skilled in the art in light of the functionality and particular chemistry use to construct the compounds. Examples of suitable protecting groups are described, for example, in Greene and Wutz, Protecting Groups in Organic Synthesis, $2^{nd}$ edition, John Wiley and Sons, New York, N.Y. (1991). Exemplary protecting groups useful in the practice of the invention in tert-butoxycarbonyl (BOC), tert-butyldimethylsily (TBDMS), trimethylsilyl (TMS), and the like.

EXAMPLES

In the examples described below, unless otherwise indicated all temperatures are set forth in degrees Celsius and all parts and percentages are by weight. Reagents were purchased from commercial suppliers such as Aldrich Chemical Company or Lancaster Synthesis Ltd. and were used without further purification unless otherwise indicated. Tetrahydrofuran (THF) and N,N-dimethylformamide (DMF) were purchased from Aldrich in Sure seal bottles and used as received. All solvents were purified using standard methods readily known to those skilled in the art, unless otherwise indicated.

The reactions set forth below were done generally under a positive pressure of nitrogen, argon or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed on glass-backed silica gel 60 F 254 plates from Analtech (0.25 mm) and eluted with the appropriate solvent ratios (v/v), and are denoted where appropriate. The reactions were assayed by TLC, NMR or HPLC and terminated as judged by the consumption of starting material.

Visualization of the TLC plates was done with a UV lamp, iodine, or p-anisaldehyde spray reagent or phosphomolybdic acid reagent (Aldrich Chemical 20 wt % in ethanol) and activated with heat. Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ prior to filtration and evaporation of the solvents under reduced pressure on a rotary evaporator and noted as solvents removed in vacuo. Flash column chromatography (Still et al., J. Org. Chem., 43, 2923 (1978)) was done using Merck EM flash silica gel (47–61 μm) and a silica gel:crude material ratio of about 20:1 to 50:1 unless otherwise stated. Hydrogenolysis was done at the pressure indicated in the examples or at ambient pressure.

$^1$H-NMR spectra were recorded on a Bruker instrument operating at 300 MHz and $^{13}$C-NMR spectra were recorded operating at 75 MHz. NMR spectra were obtained as $CDCl_3$ solutions (reported in ppm), using chloroform as the reference standard (7.25 ppm and 77.00 ppm) or $CD_3OD$ (3.4 and 4.8 ppm and 49.3 ppm), or internally tetramethylsilane (0.00 ppm) when appropriate. Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Infrared (IR) spectra were recorded on a Perkin-Elmer F-IR Spectrometer as neat oils, as KBr pellets, or as $CDCl_3$ solutions, and when given are reported in wave numbers ($cm^{-1}$). The mass spectra were obtained using LSIMS or electrospray. All melting points (mp) are uncorrected.

Unless otherwise indicated, the starting materials are commercially available or can be obtained using general techniques known in the art.

EXEMPLARY COMPOUNDS

Example 1(a)

Phenyl-(5-thiophen-2-yl-1H-pyrazol-3-yl)-amine (Compound A)

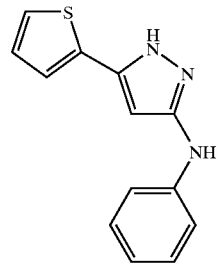

2-Acetylthiophene (0.93 mL, 8.6 mmol) and phenyl isothiocyanate (1.03 mL, 8.6 mmol) were stirred in dry DMF (6 mL) at 0° C. Sodium hydride (380 mg, 9.5 mmol, 60% in mineral oil) was added, and the reaction stirred 1.5 h at r.t. (until all gas evoluation had ceased). Iodomethane (590 μL, 9.4 mmol) was added, and the reaction stirred for 1 h before it was concentrated in vacuo. The residue was dissolved in ether (60 mL), washed before it was concentrated in vacuo. The residue was dissolved in ether (60 mL), washed with $H_2O$ (30 mL) and brine (30 mL), dried ($Na_2SO_4$), and concentrated to a yellow oil.

This crude N,S-acetal was dissolved in ethanol (15 mL). Hydrazine hydrate (625 μL 12.9 mmol) was added, and reaction was allowed to stir reflux for 16 h. It was then concentrated in vacuo and purified by silical gel chromatography (50% EtOAc/Hex). Precipitation from 2:1 $CHCl_3$/hexanes and collection by filtration gave 720 mg (35% yield) of Compound A as a white solid.

$^1$H NMR (300 MHz, DMSO-$d_6$) δ12.43 (s, 1H), 8.42 (s, 1H), 7.44 (br s, 1H), 7.40 (s, 1H), 7.32 (br s, 2H), 7.18 (t, 2H, J=7.8 Hz), 7.11 (s, 1H), 6.72 (t, 1H, J=6.9 Hz), 6.05 (s, 1H). Anal. ($C_{13}H_{11}N_3S$) C, H, N, S. Calculated C=64.71; H=4.59; N=17.41; S=13.29; found C=64.67; H=4.53; N=17.28; S=13.38. See Vishwakarma et al., Indian J. Chem vol. 24B, pp. 472–476 (1985) for a related procedure, which is incorporated herein by reference.

Example 1(b)

(5-Benzo[b]thiophen-3-yl)-1H-pyrazol-3-yl)-phenyl-amine (Compound B)

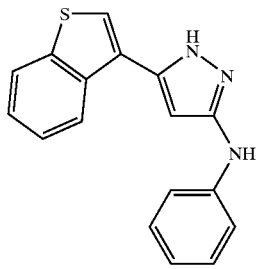

Prepared in 35% yield from 3-acetylbenzo[b]thiophene and phenyl isothiocyanate analogous to the procedure for Example 1(a). $^1$H NMR (300 MHz, DMSO-d$_6$) δ12.44 (s, 1H), 8.48 (s, 1H), 8.07 (d, 2H, J=7.5 Hz), 8.00 (s, 1H), 7.37–7.52 (m, 4H), 7.20 (t, 2H, J=7.8 Hz), 6.73 (t, 1H, J=7.2 Hz), 6.28 (s, 1H). Anal. (C$_{17}$H$_{13}$N$_3$S) C, H, N, S. Calculated C=70.08; H=4.50; N=14.32; S=11.00; found C=69.91; H=4.64; N=14.32; S=11.04.

Example 1(c)

Phenyl-(5-pyridin-3-yl)-1H-pyrazol-3-yl)-amine (Compound C)

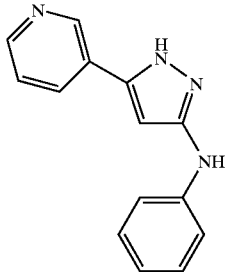

Prepared in 46% yield from 3-acetylpyridine and phenyl isothiocyanate analogous to the procedure for Example 1(a). $^1$H NMR (500 MHz, DMSO-d$_6$) δ12.59 (s, 1H), 8.97 (s, 1H), 8.52 (d, 1H, J=2.4 Hz), 8.48 (s, 1H), 8.10 (d, 1H, J=4.8), 7.46 (s, 1H), 7.36 (br s, 2H), 7.18 (t, 2H, J=7.5 Hz), 6.72 (t, 1H, J=7.0 Hz), 6.39 (s, 1H). Anal (C$_{14}$H$_{12}$N$_4$ · 0.1 H$_2$O) C, H, N. Calculated C=70.63; H=5.17; N=23.53; found C=70.93; H=5.22; N=23.45.

Example 1(d)

(1,8-Dihydro-indeno[2,1-c]pyrazol-3-yl)-phenyl-amine (Compound D)

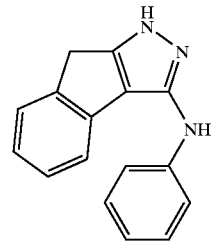

Prepared in 26% yield from freshly distilled 2-indanone and phenyl isothiocyanate analogous to the procedure for Example 1(a). $^1$H NMR (300 MHz, DMSO-d$_6$) δ12.23 (br s, 1H), 8.35 (s, 1H), 7.38 (d, 1H, J=7.2 Hz), 6.97–7.23 (m, 7H), 6.76 (t, 1H, J=7.2 Hz), 3.69 (s, 2H). Anal. (C$_{19}$H$_{15}$N$_3$) C, H, N. Calculated C=77.71; H=5.30; N=16.99; found C=77.48; H=5.38; N=16.98.

Example 1(e)

[5-(4-Bromo-thiophen-3-yl)-1H-pyrazol-3-yl]1-phenyl-amine (Compound E)

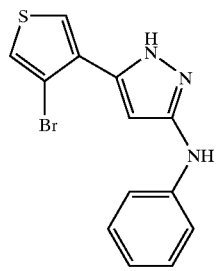

Prepared in 43% yield from 4-acetyl-3-bromo-thiophene and phenyl isothiocyanate analogous to the procedure for Example 1(a). $^1$H NMR (300 MHz, DMSO-d$_6$) δ12.31 (s, 1H), 8.47 (s, 1H), 7.83–7.86 (m, 2H), 7.32 (br s, 2H), 7.17 (t, 2H, J=7.8 Hz), 6.70 (t, 1H, J=7.2 Hz), 6.28 (s, 1H). Anal. (C$_{13}$H$_{10}$BrN$_3$S) C, H, N, S. Calculated C=48.76; H=3.15; N=13.12; S=10.01; found C=49.01; H=3.12; N=12.93; S=10.21.

4-Acetyl-3-bromo-thiophene

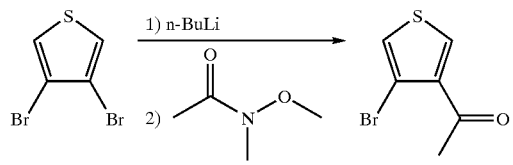

3,4)-Dibromo-thiophene (1.5 mL, 13.6 mmol) was stirred in dry ether (3( mL) at −78° C. under argon. n-Butyllithium (6.0 mL, 2.5 M solution in hexanes, 14.9 mmol) was added dropwise. The reaction was stirred for 20 min, and N-methoxy-N-methyl-acetamide (1.66 mL. 16.3 mmol) in ether (2 mL) was added. The reaction stirred for 30 min at −78° C. and then 30 min while warming to r.t. Organics were washed with 1 N HCl, H$_2$O, saturated NaHCO$_3$, and brine (15 mL each), dried (Na$_2$SO$_4$), and concentrated in vacuo. Purification by silica gel chromatography (20% to 30% EtOAc/hexanes) gave 1.69 g (61%) of 4-acetyl-3-bromo-thiophene as a faintly yellow oil. $^1$H NMR (300 MHz, CDCl3) δ8.02 (d, 1H, J=3.6 Hz), 7.32 (d, 1H, J=3.6 Hz), 2.61 (s, 1H).

Example 1(f)

Phenyl-[5-(4-trans-styryl-thiophen-3-yl]-1H-pyrazol-3-yl]-amine (Compound F)

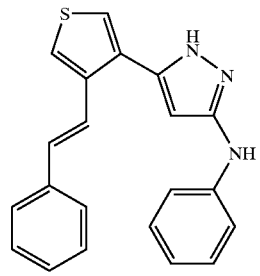

Prepared in 51% yield from 3-acetyl-4-trans-styryl-thiophene and phenyl isothiocyanate analogous to the procedure for Example 1(a). $^1$H NMR (300 MHz, DMSO-d$_6$) δ12.28 (s, 1H), 8.45 (s, 1H), 7.88 (d, 1H, J=3.0 Hz), 7.73 (d, 1H, J=3.0 Hz), 7.53 (d, 2H, J=7.2 Hz), 7.08–7.40 (m, 9H), 6.71 (t, 1H, J=7.2 Hz), 5.97 (s, 1H). Anal. (C$_{21}$H$_{17}$N$_3$S.0.5 H$_2$O) C, H, N, S. Calculated C=71.56; H=5.15; N=11.92; S=9.10; found C=71.62; H=5.18; N=11.95; S=9.09.

3-Acetyl-4-(trans-styryl)-thiophene

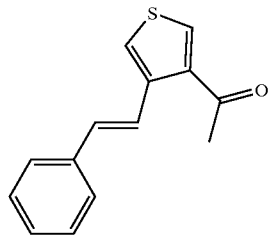

Prepared from 3-bromo-4-(trans-styryl)-thiophene (See Munro et al., *J. Chem. Soc. Perkin. Trains.*, vol. 1, pp. 1718–1723 (1980), incorporated herein by reference), in 51% yield analogous to the procedure for the preparation of 4-acetyl-3-bromo-thiophene. $^1$H NMR (300 MHz, CDCl$_3$) δ8.02 (d, 1H, J=3.0 Hz), 7.81 (dd, 1H, J=16.2, 0.6 Hz), 7.53 (d, 2H, J=7.2 Hz), 7.44 (dd. 1H, J=3.0, 0.6 Hz), 7.35 (t, 2H, J=7.2 Hz), 7.24–7.28 (m, 1H), 6.95 (d, 1H, J=16.2 Hz), 2.58 (s, 3H).

Example 1(g)

[5-(4-Cyclohex-1-enyl-thiophen-3-yl)-1H-pyrazol-3-yl]-phenyl-amine (Compound G)

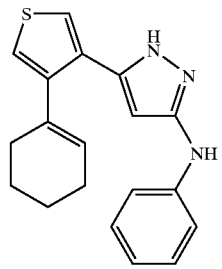

Prepared in 28% yield from 3-acetyl-4-cyclohex-1-enyl-thiophene and phenyl isothiocyanate analogous to the procedure for Example 1(a). $^1$H NMR (300 MHz, DMSO-d$_6$) δ12.12 (s, 1H), 8.40 (s, 1H), 7.65 (d, 1H, J=3.3 Hz), 7.30 (app d, 3H, J=3.0 Hz), 7.16 (d, 2H, J=7.8 Hz), 6.69 (t, 1H, J=7.2 Hz), 5.92 (s, 1H), 5.67 (s, 1H), 2.10 (s, 4H), 1.64 (br s, 4H). Anal. (C$_{19}$H$_{19}$N$_3$S) C, H, N, S. Calculated C=71.00; H=5.96; N=13.07; S=9.97; found C=70.77; H=5.94; N=12.90, S=10.01. MS (Electrospray) [M+H]/z Calculated 322; found 322.

3-Acetyl-4-cyclohex-1-enyl-thiophene

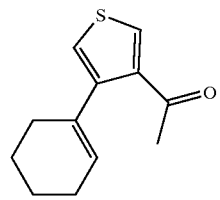

Prepared from 3-bromo-4-cyclohex-1-enyl-thiophene (See MacDowell; Jeffries *J. Org. Chem.*, 1970, 35, 871–875 incorporated herein by reference), in 31% yield analogous to the procedure for the preparation of 4-acetyl-3-bromo-thiophene. $^1$H NMR (300 MHz, CDCl$_3$) δ7.90(d, 1H, J=2.7 Hz), 6.97 (d, 1H, J=2.7 Hz), 5.66 (q, 1H, J=1.8 Hz), 2.49 (s, 3H), 2.15–2.19 (m, 4H), 1.64–1.79 (m, 4H).

Example 1(h)

[5-(4-Cyclohexyl-thiophen-3-yl)-1H-pyrazol-3-yl]-phenyl-amine (Compound H)

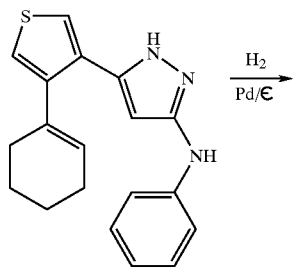

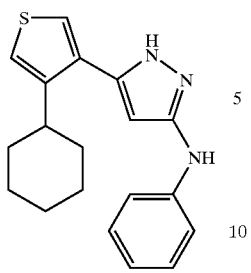

Hydrogenation of [5-(4-cyclohex-1-enyl-thiophen-3-yl)-1-H-pyrazol-3-yl]-phenylamine (50 mg, 0.156 mmol) was carried out using 10% palladium on activated carbon (~20 mg) in methanol (5 mL) and acetic acid (0.5 mL) under a balloon of hydrogen. After stirring for 16 h, the reaction was filtered through Celite. The filtrate was diluted with ether (50 mL), washed with saturated NaHCO$_3$ solution (2×25 mL) and brine (25 mL), dried (Na$_2$SO$_4$), and concentrated in vacuo. Purification by silica gel chromatography gave 29 mg (58%) of [5-(4-cyclohexyl-thiophen-3-yl)-1-H-pyrazol-3-yl]-phenylamine as a white solid.

$^1$H NMR (300 MHz, DMSO-d$_6$) δ12.13 (s, 1H), 8.43 (s, 1H), 7.62 (d, 1H, J=3.3 Hz), 7.33 (br s, 2H), 7.30 (d, 1H, J=2.4 Hz), 7.17 (d, 2H, J=7.8 Hz), 6.70 (t, 1H, J=7.2 Hz), 5.94 (s, 1H), 2.72–2.79 (m, 1H), 1.68–1.83 (m, 5H), 1.26–1.37 (m, 5H). Anal. (C$_{19}$H$_{21}$N$_3$S0.67 H$_2$O) C, H, N, S. Calculated C=68.01; H=6.7 1; N=12.52; S=9.56; found C=68.06; H=6.70; N=12.31; S=9.40. MS (Electrospray) [M+H]/z Calculated 324; found 324.

Example 1(i)

Phenyl-[5-(4-phenylsulfanyl-thiophene-3-yl)-1H-pyrazol-3-yl]-amine (Compound I)

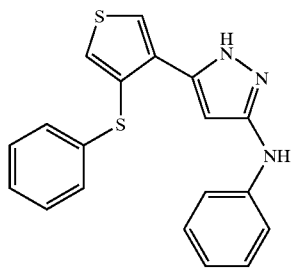

Prepared in 35% yield from 3-acetyl-4-phenylsulfanyl-thiophene and phenyl isothiocyanate analogous to the procedure of Example 1(a). $^1$H NMR (300 MHz, DMSO-(d$_6$) δ12.29 (s, 1H), 8.37 (s, 1H), 8.00 (d, 1H, J=3.3 Hz), 7.90 (s, 1H), 7.30 (t, 2H, J=7.8 Hz), 7.07–7.17 (m, 7H), 6.67 (t, 1H, J=7.2 Hz), 6.23 (s, 1H). Anal. (C$_{19}$H$_{15}$N$_3$S$_2$) C, H, N, S. Calculated C=67.27; H=4.70; N=13.07; S=9.98; found C=67.01; H=4.78; N=13.11; S=10.02.

3-Bromo-4-phenylsulfanyl-thiophene

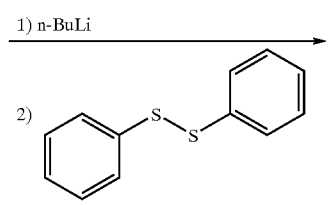

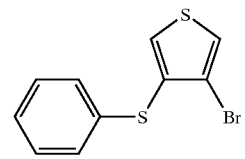

n-Butyllithium (5.0 mL, 2.5 M in hexanes, 12.5 mmol) was stirred in dry ether (12 mL) at −78° C. under argon. 3,4-Dibromo-thiophene (1.25 mL, 11.3 mmol) in ether (1 mL) was added dropwise, and the reaction stirred 25 min. Phenyldisulfide (2.73 g, 12.5 mmol) in ether (15 mL) was added slowly, and the reaction stirred 1 h at −78° C. and then 2 h at 0° C. The reaction was quenched with saturated NH$_4$Cl solution (15 mL), and organics were extracted and washed with brine (15 mL), dried (Na$_2$SO$_4$), and concentrated in vacuo. Purification by silica gel chromatography (1% to 10% ether/hexanes) gave 2.57 g (84%) of 3-bromo-4-phenylsulfanyl-thiophene as a clear oil. $^1$H NMR (300 MHz, CDCl$_3$) δ7.38 (d, 1H, J=3.3 Hz), 7.32 (d, 1H, J=3.3 Hz), 7.21–7.30 (m,5H).

4-Acetyl-3-phenylsulfanyl-thiophene

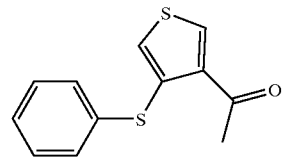

Prepared from 3-bromo-4-phenylsulfanyl-thiophene in 66% yield according to the procedure for the preparation of 4-acetyl-3-bromo-thiophene. $^1$H NMR (300 MHz, CDCl$_3$) δ8.09 (d, 1H, J=3.3 Hz), 7.57 (d, 2 H, J=7.2 Hz), 7.38–7.42 (m, 3H), 6.31 (d, 1H, J=3.3 Hz), 2.57 (s, 3H).

[5-(N-BOC-indol-3-yl)-1H-pyrazol-3-yl]-phenyl-amine

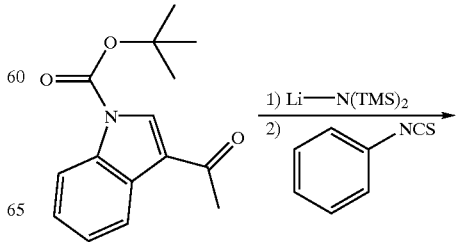

31
-continued

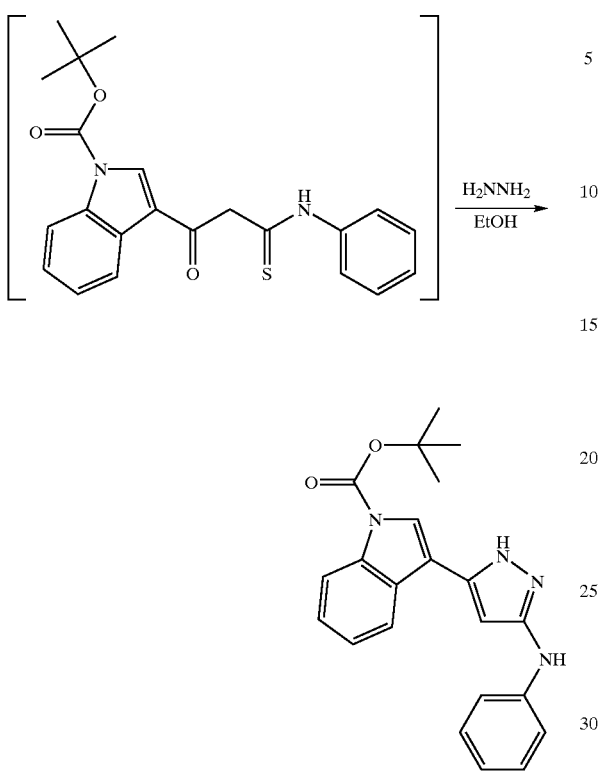

Lithium bis(trimethylsilyl)amide (2.71 mL, 1.0 M in THF, 2.71 mmol) was stirred in dry THF (15 mL), at −78° C. under argon. N-BOC-3-acetyl-indole (See Danheiser, R. L.; Brisbois, R. G.; Kowalczyk, J. J; Miller, R. F. *J. Amer. Chem. Soc.,* vol. 112, pp. 3093–3100 (1990) incorporated herein by reference), (586 mg, 2.26 mmol) in THF (10 mL) was added slowly, and the reaction stirred 30 min. Phenyl isothiocyanate (325 µL, 2.71 mmol) was added, and the reaction stirred 1 h while warming to r.t. The orange solution was poured over saturated NH₄Cl solution (30 mL) and extracted with ether (2× 30 mL). Organics were washed with brine (30 mL), dried (Na₂SO₄), and concentrated in vacio.

This crude thioamide was dissolved in ethanol (20 mL). Hydrazine hydrate (180 µL, 2.1 mmol) and HOAc (5 drops) were added, and the reaction was allowed to stir at reflux for 2 h before it was concentrated in vacuo. Purification by silica gel chromatography (30% to 50% EtOAc/hexanes) gave 499 mg (59%) of [5-(N-BOC-indol-3-yl)-1H-pyrazol-3-yl]-phenyl-amine as a faintly yellow foam. $^1$H NMR (300 MHz, DMSO-$d_6$) $\delta$12.39 (s, 1H), 8.41 (s, 1H), 8.13 (d, 2H, J=7.8 Hz), 7.87 (br s, 1H), 7.35–7.44 (m, 3H), 7.19 (t, 2H, J=7.8 Hz), 6.72 (t, 1H, J=6.9 Hz), 6.31 (s, 1H), 1.66 (s, 9H). Anal. ($C_{22}H_{22}N_4O_2 \cdot 0.4\ H_2O$) C, H, N. Calculated C=69.24.78; H=6.02; N=14.68; found C=69.27; H=6.03; N=14.63.

32

Example 1(j)
[5-(1H-Indol-3-yl)-1H-pyrazol-3-yl]-phenyl-amine
(Compound J)

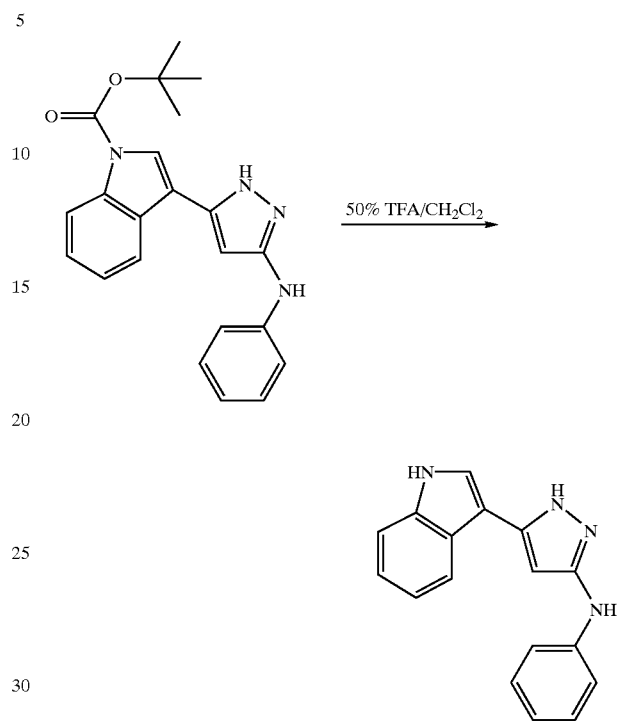

[5-(N-BOC-indol-3-yl)-1H-pyrazol-3-yl]-phenyl-amine (332 mg, 0.89 mmol) was stirred in 50% TFA/CH₂C₁₂ (8 mL) at r.t. for 1 h, at which point material had precipitated to a solid block. Solvents were removed in vacuo, and the solid was dissolved in EtOAc (50 mL), washed with saturated NaHCO₃ (25 mL) and brine (25 mL), dried (MgSO₄) and concentrated in vacIto. Purification by silica gel chromatography (50% to 70% EtOAc/hexanes) gave 182 mg (75%) of [5-(1H-indol-3-yl)-1H-pyrazol-3-yl]-phenyl-amine as a white solid. $^1$H NMR (300 MHz, DMSO-$d_6$) $\delta$12.06 (s, 1H), 11.41 (s, 1H), 8.38 (s, 1H), 7.80 (d, 1H, J=6.3 Hz), 7.74 (d, 1H, J=2.7 Hz), 7.36–7.47 (m, 3H), 7.11–7.21 (m, 4H), 6.70 (t, 1H, J=7.2 Hz), 6.14 (s, 1H). Anal. ($C_{17}H_{14}N_4 \cdot 0.05\ H_2O$) C, H, N. Calculated C=74.19; H=5.16; N=20.36; found C=74.25; H=5.17; N=20.24.

Example 2(a)
(5-Benzo[b]thiophen-3-yl-1H-pyrazol-3-yl)-4-(methoxy-phenyl)-amine (Compound K)

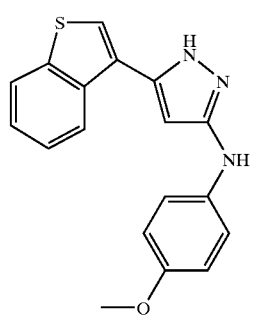

Prepared in 47% yield from 3-acetylbenzothiophene and 4-methoxy-phenyl isothiocyanate according to the procedure for Example 1(a). $^1$H NMR (300 MHz, DMSO-$d_6$) δ12.30 (s, 1H), 8.19 (s, 1H), 8.07 (d, 2H, J=7.2 Hz), 7.97 (s, 1H), 7.43–7.49 (m, 2H), 7.27 (br s, 2H), 6.82 (d, 2 H. J=9.0 Hz), 6.20 (s, 1H), 3.68 (s, 3H). Anal. ($C_{19}H_{15}N_3S_2$) C, H, N, S. Calculated C=65.30; H=4.33; N=12.02; S=18.35; found C=65.18; H=4.36; N=11.89; S=18.16.

Example 2(b)

4-(Benzo[b]thiophen-3-yl-1H-pyrazol-3-ylamino)-phenol (Compound L)

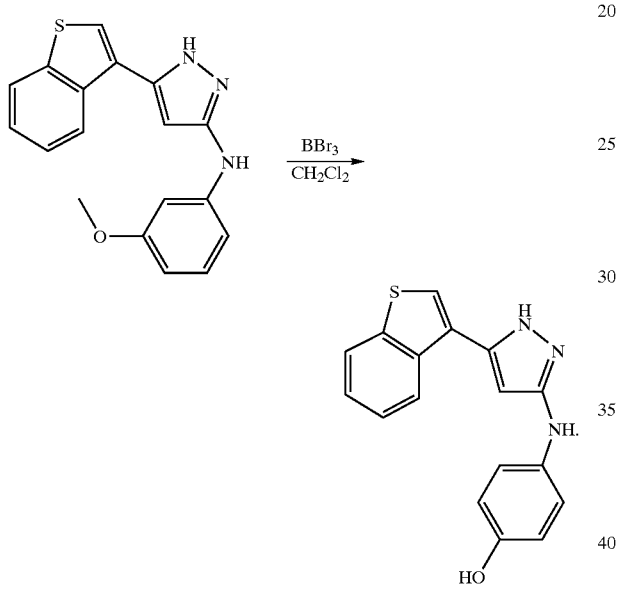

[5-(3-Benzo[b]thiophenyl)-1-H-pyrazol-3-yl]-4-methoxy-phenylamine (400 mg, 1.25 mmol) was stirred in dry $CH_2Cl_2$ (10 mL) at −78° C. Boron tribromide (2.59 mL, 1.0 M in $CH_2Cl_2$, 2.59 mmol) was added, and the reaction stirred 16 h while warming to r.t. The reaction was quenched with 0.1 N HCl (10 mL). stirring for 15 min. It was then neutralized with saturated $NaHCO_3$ and extracted with $CHCl_3$ (50 mL). Organics were washed with brine (25 mL), dried ($MgSO_4$), and concentrated in vacuo. Purification by silica gel chromatography (60% EtOAc/hexanes) gave 121 mg (32%) of 4-(benzo[b]thiophen-3-yl-1H-pyrazol-3-ylamino)-phenol as a white solid.

$^1$H NMR (300 MHz, DMSO-$d_6$) δ12.22 (s, 1H), 8.71 (s, 1H), 7.95–8.06 (m, 4H), 7.40–7.50 (m, 2H), 7.15 (br s, 1H), 6.65 (d, 2 H, J=9.0 Hz), 6.18 (s, 1H). Anal. ($C_{17}H_{13}N_3OS$) C, H. N, S. Calculated C=66.43; H=4.26; N=13.67; S=10.43; found C=66.28; H=4.27; N=13.38; S=10.43.

Example 2(c)

(5-Benzo[b]thiophen-3-yl)-1H-pyrazol-3-yl)-3-(methoxy-phenyl)-amine (Compound M)

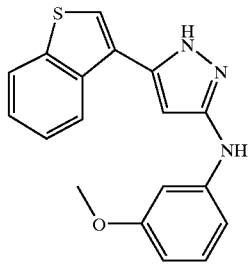

Prepared in 40% yield from 3-acetylbenzo[b]thiophene and 3-methoxy-phenyl isothiocyanate analogous to the procedure for Example 1(a). $^1$H NMR (300 MHz, DMSO-$d_6$) δ12.48 (s, 1H), 8.51 (s, 1H), 7.99–8.08 (m, 3H), 7.42–7.52 (m, 2H), 7.09 (t, 2H, J=7.8 Hz), 6.88 (br s, 1H), 6.23–6.37 (m, 2H), 3.71 (s, 3H). Anal. ($C_{18}H_{15}N_3OS·0.5 H_2O$) C, H, N, S. Calculated C=65.43; H=4.88; N=12.72; S=9.70; found C=65.65; H=4.86; N=12.63; S=9.85.

Example 2(d)

3-(Benzo[b]thiophen-3-yl-1H-pyrazol-3-ylamino)-phenol (Compound N)

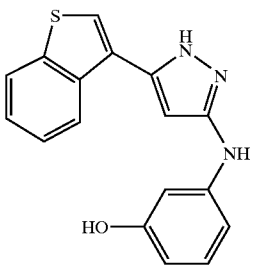

Prepared in 26% yield from (5-benzo[b]thiophen-3-yl)-1H-pyrazol-3-yl)-3-(methoxy-phenyl)-amine analogous to the procedure for 4-(benzo[b]thiophen-3-yl-1H-pyrazol-3-ylamino)-phenol [Example 2(b)]. $^1$H NMR (300 MHz, DMSO-$d_6$) δ12.40 (s, 1H), 9.09 (s, 1H), 8.33 (s, 1H), 8.06 (d, 2 H, J=6.9 Hz), 7.98 (s. 1H), 7.42–7.51 (m, 2H), 6.96 (t, 1H, J=7.8 Hz), 6.92 (br s, 1H), 6.71 (br s, 1H), 6.26 (br s, 1H), 6.15 (d, 1H, J=7.5 Hz). Anal. ($C_{17}H_{13}N_3OS·0.33 H_2O$) C, H, N, S. Calculated C=65.17; H=4.39; N=13.41; S=10.23; found C=65.30; H=4.40; N=13.05; S=10.19.

Example 2(e)

4-(5-Benzo[b]thiophen-3-yl)-1H-pyrazol-3-yl)-benzenesulfonamide (Compound O)

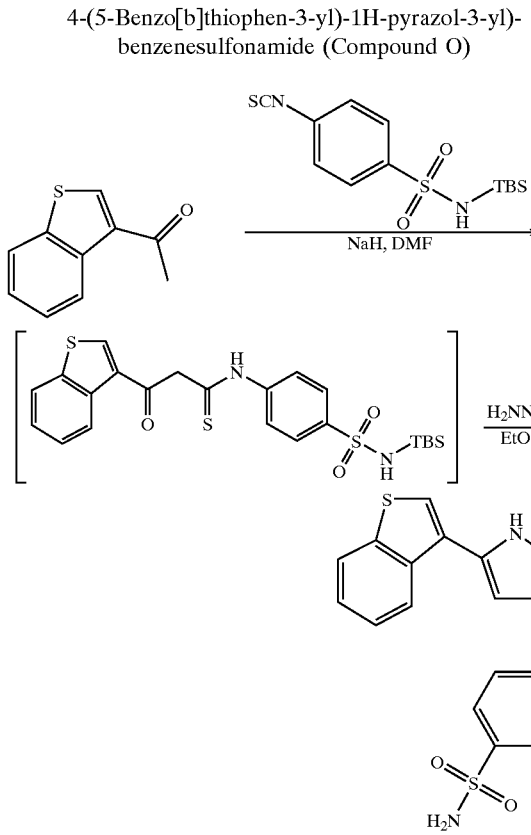

3-Acetylbenzo[b]thiophene (400 mg, 2.3 mmol) and 4-isothiocyanato-N-(TBDMS)-benzenesulfonamide (740 mg, 2.3 mmol) were stirred in dry DMF (12 mL) at 0° C. Sodium hydride (190 mg, 60% in mineral oil, 4.75 mmol) was added, and the reaction stirred 1.5 h at r.t., at which time all gas evolution had ceased. The reaction was poured over 0.1 N HCl (30 mL) and extracted with ether (2×35 mL). Organics were washed with brine (35 mL), dried ($Na_2SO_4$) and concentrated in vacuo to a yellow solid.

This crude thioamide was dissolved in ethanol (20 mL). Hydrazine hydrate (100 δL, 2.1 mmol) and HOAc (5 drops) were added, and the reaction was allowed to stir at reflux for 2 h. It was then concentrated in vacuo, and the residue was taken up in ether (40 mL). The yellow solid collected by filtration and then recrystallized from methanol to give 265 mg (32%) of 4-(5-benzo[b]thiophen-3-yl)-1H-pyrazol-3-yl)-benzenesulfonamide as a white solid. $^1$H NMR (300 MHz, DMSO-$d_6$) δ12.63 (br s, 1H), 9.08 (s, 1H), 8.08 (d, 2H, J=7.5 Hz), 8.02 (s, 1H), 7.65 (d, 2H, J=8.7 Hz), 7.43–7.51 (m, 4H), 7.06 (s, 2H), 6.35 (s, 1H). Anal. ($C_{17}H_{14}N_3O_2S_2$) C, H, N, S. Calculate C=55.12; H=3.81; N=15.12; S=17.31; found C=55.01; H=3.81; N=15.08; S=12.35.

4-Isothiocyanato-N-(TBDMS)-benzenesulfonamide

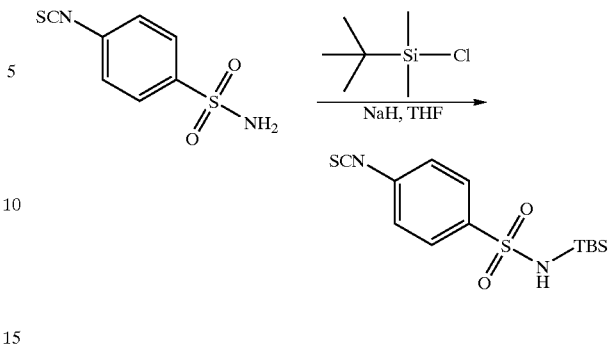

4-Isothiocyanato-benzenesulfonamide (750 mg, 3.5 mmol), and tert-butyldimethylsilyl chloride (528 mg, 3.5 mmol) stirred in dry THF (20 mL) at 0° C. Sodium hydride (210 mg, 60% in mineral oil, 5.25 mmol) was added, and the reaction stirred for 1 h before it was poured over $H_2O$ (50 mL) and extracted with ether (2×50 mL). Organics were washed with brine (25 mL), dried ($Na_2SO_4$), and concentrated in vacuo. Purification by silica gel chromatography gave 920 mg (80%) of 4-isothiocyanato-N-(TBDMS)-benzenesulfonamide as a white solid. $^1$H NMR (300 MHz, CDCl$_3$) δ7.86 (d, 2H, J=6.9 Hz), 7.31 (d, 2 H, J=6.9 Hz), 4.40 (s, 1H), 0.90 (s, 9H), 0.22 (s, 6H). Anal. ($C_{13}H_{20}N_2O_2S_2Si$) C, H, N, S. Calculated C=47.53; H=6.14; N=8.53; S=19.52; found C=47.47; H=6.25; N=8.46; S=19.49.

Example 3(a)

4-[5-(7-Bromo-benzo[b]thiophen-3-yl)-1H-pyrazol-3-ylamino]-benzenesulfonamide (Compound P)

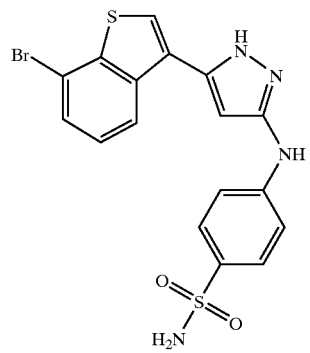

Prepared in 41% yield from 3-acetyl-7-bromo-benzo[b]thiophene and 4-isothiocyanato-N-(TBDMS)-benzenesulfonamide analogous to the procedure for 4-(5-benzo[b]thiophen-3-yl)-1H-pyrazol-3-yl)-benzenesulfonamide [Example 2(e)]. $^1$H NMR (300 MHz, DMSO-$d_6$) δ12.71 (s, 1H), 9.11 (s, 1H), 8.13 (s, 1H), 8.06 (d, 1H, J=7.2 Hz), 7.72 (d, 1H, J 7.2 Hz), 7.64 (d, 2H, J=8.7 Hz), 7.48 (br s, 3H), 7.05 (s, 2H), 6.33 (s, 1H). Anal. ($C_{17}H_{13}BrN_3O_2S_2$·0.2 EtOAc) C, H, N, S. Calculated C=45.78; H=3.15; N=12.00; S=13.73; found C=45.74; H=3.14; N=11.93; S=13.83. MS (Electrospray) [M+H]/z Calculated 449/451; found 449/451.

3-Acetyl-7-bromo-benzo[b]thiophene

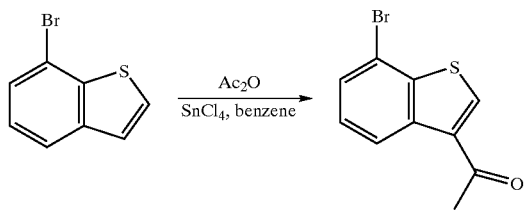

7-Bromo-benzo[b]thiophene (See Amin et al., *J. Chem Soc. Perkin Trans.*, vol. 2, pp.1489–1492 (1982), incorporated herein by reference), (2.49 g, 11.7 mmol) was stirred in benzene (25 mL) with acetic anhydride (3.31 mL, 35.1 mmol) under argon. Tin (IV) chloride (4.1 mL, 35.1 mmol) in benzene (15 mL) was added slowly, and the reaction stirred at reflux under argon for 2 h. The red solution was allowed to cool, and was poured over ice water (60 mL). Ether (100 mL) was added, and organics were separated, washed with water (50 mL), sat NaHCO$_3$ (50 mL), brine (50 mL), dried (Na$_2$SO$_4$), and concentrated in vacuo. Purification by silica gel chromatography (10% EtOAc/hexanes) gave 1.92 g (64%) of 3-acetyl-7-bromo-benzo[b]thiophene as a white solid. $^1$H NMR (300 MHz, CDCl$_3$) δ8.74 (d, 1H, J=7.8 Hz), 8.33 (s, 1H), 7.58 (d, 1H, J=7.8 Hz), 7.38 (t, 1H, J=7.8 Hz), 2.65 (s, 3H). Anal. (C$_{10}$H$_7$BrOS) C, H. Calculated C=47.08, H=2.77; found C=47.03; H=2.78. In addition, 490 mg (16%) of the more polar 2-acetyl-7-bromo-benzo[b]thiophene was isolated. $^1$H NMR (300 MHz, CDCl$_3$) □ 8.02 (s, 1H), 7.85 (d, 1H, J=7.8 Hz), 7.62 (d, 1H, J=7.8 Hz), 7.30 (t, 1H, J=7.8 Hz), 2.67 (s, 3H).

Example 3(b)

4-{5-[7-(3-Methoxy-phenyl)-benzo[b]thiophen-3-yl]-1H-pyrazol-3-ylamino]-benzenesulfonamide (Compound Q)

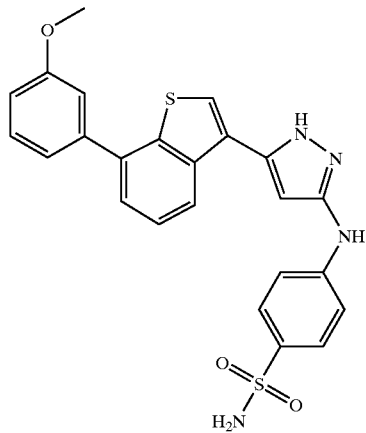

Prepared in 41% yield from 3-acetyl-7-(3-methoxy)-benzyl-benzo[b]thiophene and 4-isothiocyanato-N-(TBDMS)-benzenesulfonamide analogous to the procedure for 4-(5-benzo[b]thiophen-3-yl)-1H-pyrazol-3-yl)-benzenesulfonamide [Example 2(e)]. $^1$H NMR (300 MHz, DMSO-d$_6$) δ12.68 (s, 1H), 9.12 (s, 1H), 8.04 (s, 2H), 7.61–7.67 (m, 3H), 7.45–7.53 (m, 4H), 7.24–7.31 (m, 2H), 7.06 (br s, 3H), 6.33 (s, 1H), 3.84 (s, 3H). Anal. (C$_{24}$H$_{20}$N$_4$O$_3$S$_2$) C, H, N, S. Calculated C=60.49; H=4.23; N=11.76; S=13.45; found C=60.38; H=4.27; N=11.63; S=13.43.

3-Acetyl-7-(3-methoxy)-phenyl-benzo[b]thiophene

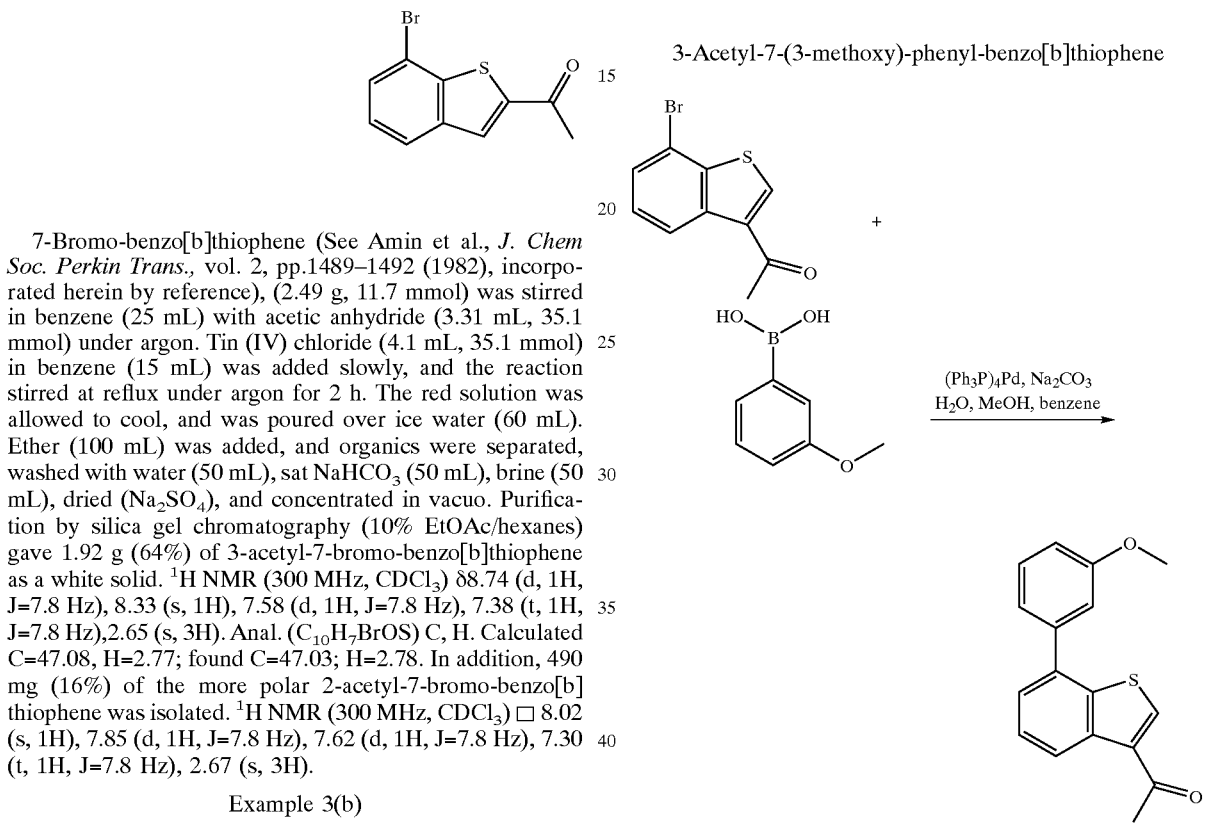

3-Acetyl-7-bromo-benzo[b]thiophene (880 mg, 3.45 mmol), 3-methoxy-phenyl boronic acid (578 mg, 3.8 mmol), and sodium carbonate (403 mg, 3.8 mmol) were stirred in benzene (20 mL), methanol (4 mL), and H$_2$O (1 mL) in a flask purged with argon. Tetrakis(triphenylphosphine)palladium(0) (300 mg, 0.26 mmol) was added, and the reaction stirred at reflux under argon for 9 h. The cooled reaction was diluted with EtOAc (50 mL), washed with H$_2$O (25 mL) and brine (25 mL), dried (Na$_2$SO$_4$), and concentrated in vacuo. Purification by silica gel chromatography (10% to 20% EtOAc/hexanes) gave 726 mg (75%) of 3-acetyl-7-(3-methoxy)-phenyl-benzo[b]thiophene as a faintly yellow solid. $^1$H NMR (300 MHz, CDCl$_3$) δ8.79 (dd, 1H, J=8.1, 1.2 Hz), 8.31 (s, 1H), 7.58 (t, 1H, J=7.8 Hz), 7.40–7.47 (m, 2H), 7.20–7.27 (m, 3H), 6.99 (dd, 1H, J=8.1, 2.1 Hz), 3.88 (s, 3H), 2.67 (s, 3H). Anal. (C$_{17}$H$_{14}$O$_2$S.0.2H$_2$O) C, H, S. Calculated C=71.40, H=5.08; S=11.21; found C=71.49; H=5.09; S=11.15.

Example 3(c)

4-{5-[7-(3-Hydroxy-phenyl)-benzo[b]thiophen-3-yl]-1H pyrazol-3-ylamino]-benzenesulfonamide
(Compound R)

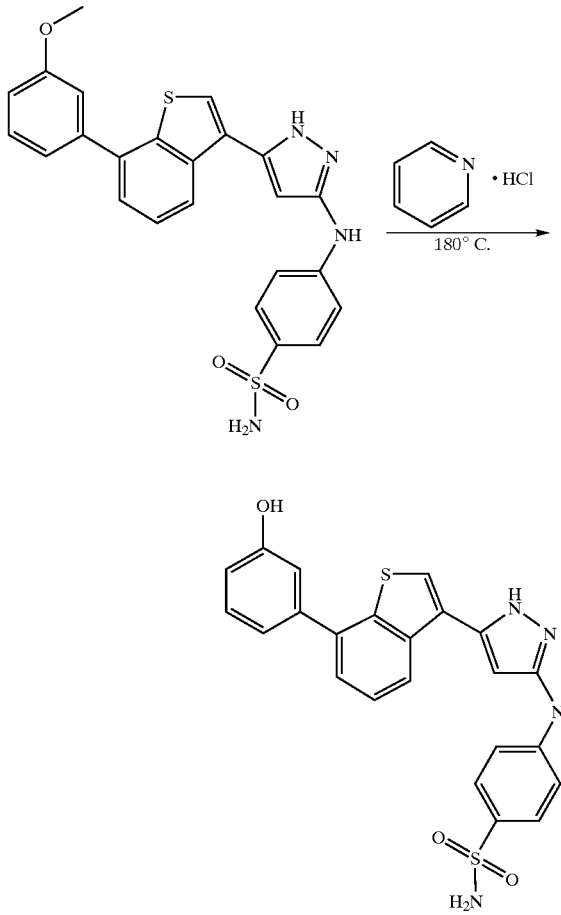

Example 3(d)

4-{5-[7-(4-Methoxy-phenyl)-benzo[b]thiophen-3-yl]-1H-pyrazol-3-ylamino]-benzenesulfonamide
(Compound S)

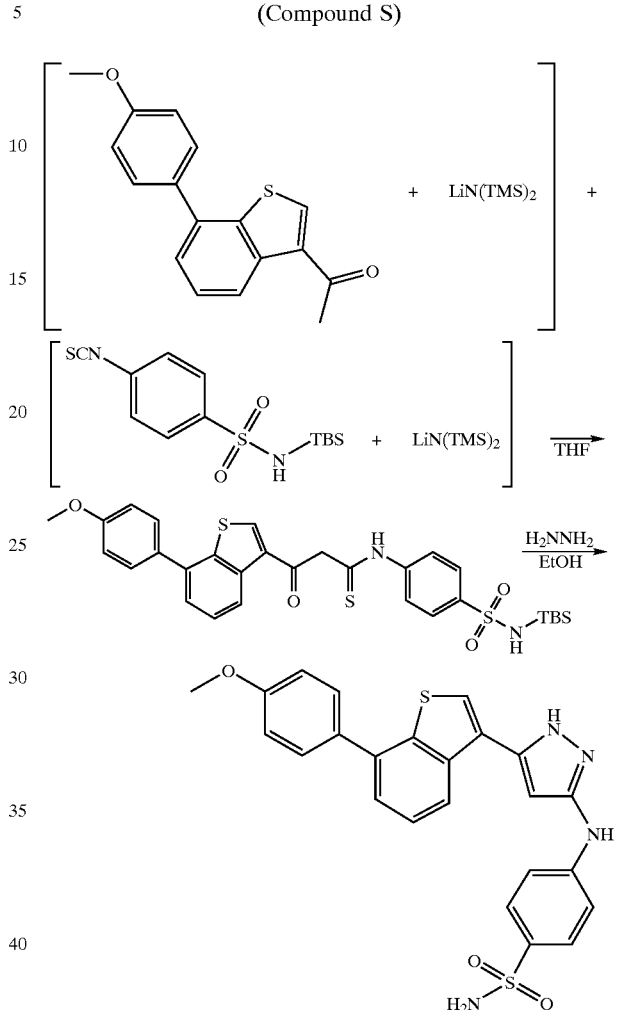

4-{5-[7-(3-Methoxy-phenyl)-benzo[b]thiophen-3-yl]-1H-pyrazol-3-ylamino]-benzenesulfonamide (130 mg, 0.27 mmol) and pyridinium chloride (1.3 g) were combined in a sealed tube and heated at 180° C. for 2 h. The reaction was cooled, quenched with saturated NaHCO$_3$ solution until the solid clump was broken up, and extracted with EtOAc (60 mL). Organics were washed with brine (25 mL), dried (Na$_2$SO$_4$), and concentrated in vacuo. Purification by silica gel chromatography gave 86 mg (68%) of 4-{5-[7-(3-hydroxy-phenyl)-benzo[b]thiophen-3-yl]-1H-pyrazol-3-ylamino]-benzenesulfonamide as a white solid. $^1$H NMR (300 MHz, DMSO-d$_6$) δ12.67 (s, 1H), 9.72 (s, 1H), 9.13 (s, 1H), 8.04 (s, 1H), 8.01 (s, 1H), 7.58–7.67 (m, 3H), 7.45–7.51 (m, 3H), 7.36 (t, 1H, J=7.8 Hz), 7.06–7.14 (m, 4H), 6.87 (d, 1H, J=7.5 Hz), 6.33 (s, 1H). Anal. (C$_{23}$H$_{18}$N$_4$O$_3$S$_2$.0.1 H$_2$O) C, H, N, S. Calculated C=59.49; H=3.95; N=12.07; S=13.81; found C=59.51; H=3.95; N=12.20; S=13.63.

Lithium bis(trimethylsilyl)amide (2.48 mL, 1.0 M in THF, 2.48 mmol) was stirred in dry THF (10 mL) at −78° C. under argon. 3-Acetyl-7-(4-methoxy)-phenyl-benzo[b]thiophene (636 mg, 2.25 mmol) in THF (8 mL) was added slowly, and the reaction stirred for 30 min. During this time, in a separate flask, 4-isothiocyanato-N-(TBDMS)-benzenesulfonamide (775 mg, 2.36 mmol) was stirred in THF (10 mL) at −78° C., and lithium bis(trimethylsilyl)amide (2.58 mL, 2.58 mmol) was added dropwise. After this stirred for 10 min, it was added via cannula to the ketone-containing flask, and the reaction stirred 1.5 h while warming to r.t. The resulting orange material was poured over 0.1 N HCl (40 mL) and extracted with ether (2×30 mL). Organics were washed with brine (25 mL), dried (Na$_2$SO$_4$), and concentrated in vacuo to a yellow foam.

This crude thioamide was dissolved in ethanol (20 mL). Hydrazine hydrate (100 μL, 2.1 mmol) and HOAc (5 drops) were added, and the reaction was allowed to stir at reflux for 2 h. It was then concentrated in vacuo and purified by silica gel chromatography (60% THF/hexanes). Precipitation from MeOH and collection by filtration gave 386 mg (36%) of 4-{5-[7-(4-methoxy-phenyl)-benzo[b]thiophen-3-yl]-1H -pyrazol-3-ylamino]-benzenesulfonamide as a white solid. $^1$H NMR (300 MHz, DMSO-$d_6$) δ12.68 (s, 1H), 9.13 (s, 1H), 8.04 (s, 1H), 8.00 (s, 1H), 7.57–7.68 (m, 5H), 7.44–7.47 (m, 3H), 7.13 (d, 2H, J=8.7 Hz), 7.07 (s, 2H), 6.34 (s, 1H), 3.84 (s, 3H). Anal. ($C_{24}H_{20}N_4O_3S_2 \cdot 0.1$ $H_2O$) C, H, N, S. Calculated C=59.49; H=3.95; N=12.07; S=13.81; found C=59.48; H=4.02; N=12.17; S=13.69.

Example 3(e)

4-{5-[7-(4-Hydroxy-phenyl)-benzo[b]thiophen-3-yl]-1H-pyrazol-3-ylamino]-benzenesulfonamide (Compound T)

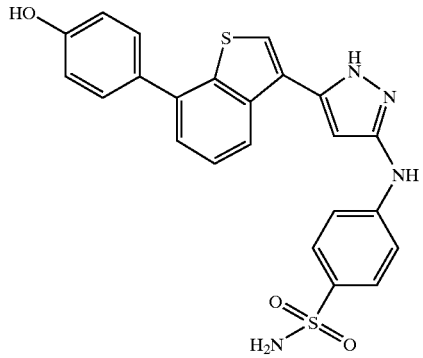

Prepared in 63% yield from 4-{5-[7-(4-methoxy-phenyl)-benzo[b]thiophen-3-yl]-1H-pyrazol-3-ylamino]-benzenesulfonamide analogous to the procedure for 4-{5-[7-(3-hydroxy-phenyl)-benzo[b]thiophen-3-yl]-1H-pyrazol-3-ylamino]-benzenesulfonamide [Example 3(c)]. $^1$H NMR (300 MHz, DMSO-$d_6$) δ12.66 (s, 1H), 9.74 (s, 1H), 9.13 (s, 1H), 8.02 (s, 1H), 7.98 (d, 1H, J=7.8 Hz). 7.65 (d, 2H, J=8.7 Hz), 7.41–7.60 (m, 6H), 7.06 (s, 2H), 6.93 (d, 2H, J=8.7 Hz), 6.33 (s, 1H). Anal. ($C_{23}H_{18}N_4O_3S_2$) C, H, N, S. Calculated C=60.49; H=4.23; N=11.76; S=13.45; found C=60.27; H=4.27; N=11.79; S=13.39.

Example 3(f)

{5-[3-(5-Bromo)-benzo[b]Thiophenyl]-1-H-pyrazol-3-yl}-phenylamine-4-Sulfonamide (Compound U)

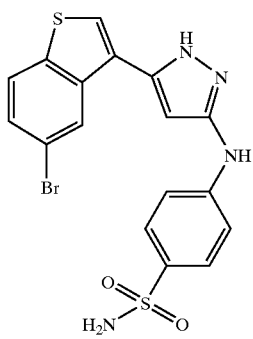

Prepared in 26% yield from 3-acetyl-5-bromo-benzothiophene and 4-isothiocyanato-N-(TBDMS)-benzenesulfonamide analogous to the procedure for 4-(5-benzo[b]thiophen-3-yl)-1H-pyrazol-3-yl)-benzenesulfonamide [Example 2(e)]. $^1$H NMR (300 MHz, DMSO-$d_6$) δ12.69 (s, 1H), 9.13 (s, 1H), 8.04–8.13 (m, 3H), 7.47–7.68 (m, 5H), 7.06 (s, 2H), 6.31 (s, 1H). Anal. ($C_{17}H_{13}BrN_4O_2S_2 \cdot 0.4H_2O$) C, H, N, S. Calculated C=44.72, H=3.05, N=12.27, S=14.05; found C=44.61, H=3.06, N=12.30, S=14.15.

3-Acetyl-5-Bromo-benzo[b]Thiophene

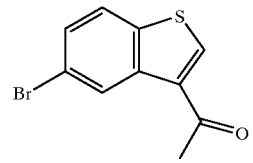

Prepared in 70% yield from 5-bromo-benzothiophene (See Ple, P. A.; Marnett, L. J. J. Heterocycl. Chem., vol. 25, pp. 1271–1272 (1988), incorporated herein by references), analogous to the procedure for the preparation of 3-acetyl-7-bromo-benzo[b]thiophene. $^1$H NMR (300 MHz, CDCl$_3$) δ8.04 (d, H. J=1.8Hz), 7.86 (s, 1H), 7.74 (d, 1H, J=8.4Hz), 7.56 (dd, 1H, J=8.4, 1.8Hz), 2.67 (s, 3H). Anal. ($C_{10}H_7BrOS$) C, H, Br, S. Calculated C=47.07, H=2.77, Br=31.32, S=12.57; found C=47.18, H=2.76, Br=31.42, S=12.55.

Example 3(g)

4-[5-(6-Methoxy-benzo[b]Thiophen-3-yl)-1H-pyrazol-3-ylamino]-Benzenesulfonamide (Compound V)

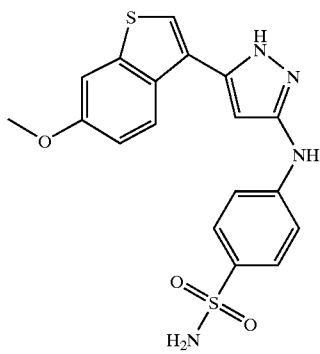

Prepared in 34% yield from 3-acetyl-6-methoxy-benzolblthiophene and 4-isothiocyanato-N-(TBDMS)-benzenesulfonamide analogous to the procedure for 4-{5-[7-(4-methoxy-phenyl)-benzo[b]thiophen-3-yl]-1H-pyrazol-3-ylamino]-benzenesulfonamide [Example 3(d)]. $^1$H NMR (300 MHz, DMSO-$d_6$) 6 12.60 (s, 1H), 9.10 (s, 1H), 7.92 (d, 1H, J=8.7Hz), 7.80 (s, 1H), 7.65 (app d, 3H, J=8.7Hz), 7.48 (d, 2H, J=8.1Hz), 7.12 (d, 1H, J 8.7Hz), 7.05 (s, 2H), 6.28 (s, 1H), 3.85 (s, 3H). Anal. ($C_{18}H_{16}N_4O_3S_2 \cdot 0.35$ $H_2O$) C. H, N, S. Calculated C=53.15, H=4.14, N=11.77, S=15.77; found C=53.50, H=4.14, N=13.77, S=15.77.

6-Methoxy-benio[b]Thiophene-3-Carboxylic Acid Methoxy-methyl Amide

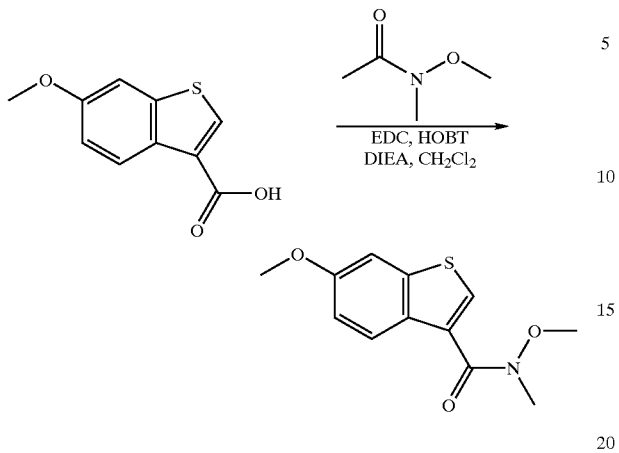

6-Methoxy-benzo[b]thiophene-3-carboxylic acid (See Titus, R. L.; Titus, C. F. *J. Heterocycl. Chem.*, 1973, 10, 679–681, incorporated herein by references), (1.2 g, 5.77 mmol) was stirred in dry $CH_2Cl_2$ (50 mL) with N,O-dimethyl-hydroxylamine hydrochloride (620 mg, 6.35 mmol). HOBT (1.54 g, 8.08 mmol), EDC (1.54 g, 8.08 mmol), and DIEA (2.16 mL, 12.11 mmol) were added, and the reaction stirred 3 h at r.t. The reaction was diluted with $CHCl_3$ (50 mL) and washed with $H_2O$, 1 N HCl, $H_2O$, saturated $NaHCO_3$, and brine (25 mL each). Organics were dried ($Na_2SO_4$) and concentrated in vacuo. Purification by silica gel chromatography (30% to 50% EtOAc/hexanes) gave 952 mg (66%) of 6-methoxy-benzo[b]thiophene-3-carboxylic acid methoxy-methyl amide as a clear oil. $^1$H NMR (300 MHz, $CDCl_3$) δ8.11 (d, 1H, J=9.0 Hz), 7.89 (s, 1H), 7.31 (d, 1H, J=2.4Hz), 7.06 (dd, 1H, J=9.0, 2.4Hz), 3.88 (s, 3H), 3.61 (s, 3H). 3.40 (s, 3H). Anal. ($C_{12}H_{13}NO_3S$) C, H, N. Calculated C=57.39, H=5.21, N=5.57; found C=57.39, H=5.11, N=5.57.

3-Acetyl-6-Methoxy-benzo[b]Thiophene

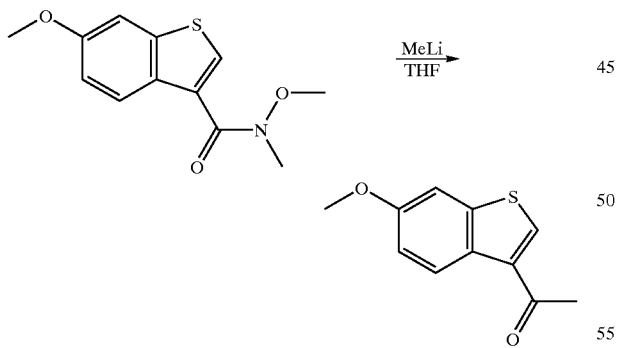

6-Methoxy-benzo[b]thiophene-3-carboxylic acid methoxy-methyl amide (800 mg, 3.19 mmol) was stirred in dry THF (20 mL) under argon at −78° C. under argon. Methyl lithium (5.0 mL, 1.5 M in hexanes, 2.35 mmol) was added dropwise, and the reaction stirred 1 h at −78° C. and then 1 h while warning to −20° C. The reaction was poured over saturated $NH_4Cl$ (40 mL) and extracted with EtOAc (2×30 mL). Organics were washed with brine (25 mL), dried ($Na_2SO_4$), and concentrated in vacuo. Purification by silica gel chromatography gave 234 mg (36%) of 3-acetyl-6-methoxy-benzo[b]thiophene as an orange solid. $^1$H NMR (300 MHz, $CDCl_3$) δ8.64 (d, 1H, J=9.0Hz), 8.11 (s, 1H), 7.30 (d, 1H, J=2.4Hz), 7.10 (dd, 1H, J=9.0, 2.4Hz), 3.89 (s, 3H), 2.63 (s, 3H) ($C_{11}H_{10}O_2S$) C, H. S. Calculated C=64.06, H=4.89, S=15.54; found C=64.31, H=4.82, S=15.50.

Example 3(h)

4-[5-(6-Hydroxy-benzo[b]Thiophen-3-yl)-1H-pyrazol-3-ylamino]-Benzenesulfonamide (Compound W)

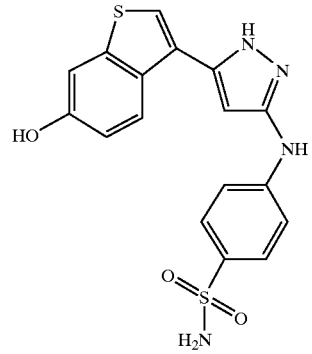

Prepared in 29% yield from 4-[5-(6-methoxy-benzo[b]thiophen-3-yl)-1H-pyrazol-3-ylamino]-benzenesulfonamide analogous to the procedure for 4-(5-[7-(3-hydroxy-phenyl)-benzo[bithiophen-3-yl]-1H-pyrazol-3-ylamino]-benzenesulfonamide [Example 3(c)]. $^1$H NMR (300 MHz, DMSO-$d_6$) δ12.58 (s, 1H), 9.77 (s, 1H), 9.08 (s, 1H), 7.82 (d, 1H, J=8.1Hz), 7.69 (s, 1H), 7.65 (d, 2H, J=8.7Hz), 7.47 (d, 2H, J=7.2 Hz). 7.36 (s, 1H), 7.05 (s, 2H), 6.98 (d, 1H, J=8.7Hz), 6.26 (s, 1H). Anal. ($C_{17}H_{14}N_4O_3S_2$ .0.3$H_2O$) C, H, N, S. Calculated C=52.11, H=3.76, N=14.30, S=16.36; found C=52.130, H=3.81, N=13.30, S 16.32.

Example 3(i)

4-[5-(1H-Indol-3-yl)-1H-pyrazol-3-ylamino]-Benzenesulfonamide (Compound X)

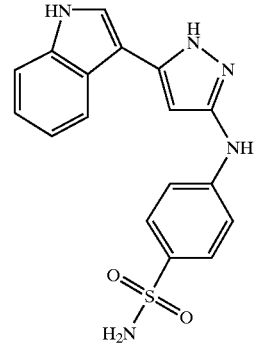

Prepared in 88% yield from 4-[5-(N-BOC-indol-3-yl)-1H-pyrazol-3-ylamino]-benzenesulfonamide analogous to the procedure for the preparation of [5-(1H-indol-3-yl)-1H-pyrazol-3-yl]-phenyl-amine [Example 1(J)]. $^1$H NMR (300 MHz, DMSO-$d_6$) δ12.27 (s, 1H), 11.44(s, 1H), 9.01 (s, 1H), 7.80 (d, 1H, J=7.2 Hz), 7.76 (d, 1H, J=2.1 Hz), 7.64, (d, 2H, J=9.0 Hz), 7.44–7.49 (m, 3H), 7.12–7.18 (m, 2H), 7.03 (s, 2H), 6.20 (s, 1H). Anal. ($C_{17}H_{15}N_5O_2S$) C, H, N, S. Calculated C=57.78, H=4.28, N=19.82, S=9.07; found C=57.67, H=4.25, N=19.58, S=9.09.

4-[5-(N-BOC-indol-3-yl)-1H-pyrazol-3-ylamino]-benzenesulfonamide

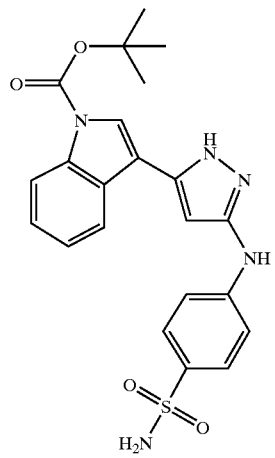

Prepared in 66% yield from 3-acetyl-N-BOC-indole (See MacDowell; Jeffries *J. Org. Chem.*, 1970, 35, 871–875, incorporated herein by reference), and 4-isothiocyanato-N-(TBDMS)-benzenesulfonamide analogous to the procedure for [5-{3-[7-(4-methoxy)-phenyl]-benzothiophenyl}-1-H-pyrazol-3-yl]-phenylamine-4-sulfonamide [Example 3(d)]. $^1$H NMR (300 MHz, DMSO-$d_6$) δ12.60 (s, 1H), 8.98 (s, 1H), 8.05 (d, 2H, J=8.1 Hz), 7.78 (s, 1H), 7.55 (d, 2H, J=8.7 Hz), 7.27–7.39 (m, 4H), 6.96 (s, 1H), 1.57 (s, 1H). Anal. ($C_{22}H_{23}N_5O_4S$) C. H, N, S. Calculated C=58.27, H=5.11, N=15.44, S=7.07; found C=57.81, H=5.12, N=15.05, S=6.89.

BIOCHEMICAL AND BIOLOGICAL EVALUATION

The exemplary compounds described above may be tested for their activity as described below. The ability of a protein kinase inhibitor to block cellular proliferation induced by growth factors is directly correlated with its ability to block receptor autophosphorylation. To measure the protein kinase inhibition activity of the compounds, the following constructs were devised.

Cyclin-dependent kinase activity was measured by quantifying the enzyme-catalyzed, time-dependent incorporation of radioactive phosphate from [$^{32}$P]ATP or [$^{33}$P]ATP into a protein substrate. Unless noted otherwise, assays were performed in 96-well plates in a total volume of 50 μL, in the presence of 10 mM HEPES (N-[2-hydroxyethyl]piperazine-N'-[2-ethanesulfonic acid]) (pH 7.4). 10 mM MgCl$_2$, 25 μM adenosine triphosphate (ATP), 1 mg/mL ovalbumin, 5 μg/mL leupeptin, 1 mM dithiothreitol, 10 mM beta-glycerophosphate, 0.1 mM sodium vanadate, 1 mM sodium fluoride, 2.5 mM ethylene glycol-bis(β-aminoethyl ethKer)-N,N,N'N'-tetraacetic acid (EGTA), 2% (v/v) dimethylsulfoxide, and 0.03–0.4 μCi [$^{32/33}$P]ATP per reaction. Reactions were initiated with enzyme, incubated at 30° C. and terminated after 20 minutes by the addition ofethyl-enediaminetetraacetic acid (EDTA) to 250 mM. The phosphorylated substrate was then captured on a nitrocellulose or phosphocellulose membrane using a 96-well filtration manifold, and unincorporated radioactivity was removed by repeated washing with 0.85% phosphoric acid. Radioactivity was quantified by exposing the dried membranes to a phosphorimager.

Apparent K$_i$ values were measured by assaying enzyme activity in the presence of different inhibitor compound concentrations and subtracting the background radioactivity measured in the absence of enzyme. Inhibition data were fit to an equation for competitive inhibition using Kaleidagraph (Synergy Software), or were fit to an equation for competitive tight-binding inhibition using the software KineTic (BioKin, Ltd.).

Inhibition of CDK4/Cyclin D Retinoblastoma Kinase Activity

A complex of human CDK4 and cyclin D3, or a complex of human CDK4 and genetically truncated (1–264) cyclin D3, was purified using traditional biochemical chromatographic techniques from insect cells that had been co-infected with the corresponding baculovirus expression vectors ((see e.g., Meijer and Kim, "Chemical Inhibitors of Cyclin-Dependent Kinases," *Methods in Enzymol,.* vol. 283, pp. 113–128 (1997)). The enzyme complex (5 or 50 nM) was assayed with 0.3–0.5 μg of purified recombinant retinoblastoma protein fragment (Rb) as a substrate. The engineered Rb fragment (residues 386–928 of the native retinoblastoma protein; 62.3 kDa) contains the majority of the phosphorylation sites found in the native 106-kDa protein, as well as a tag of six histidine residues for ease of purification. Phosphorylated Rb substrate was captured by microfiltration on a nitrocellulose membrane and quantified using a phosphorimager as described above. For measurement of tight-binding inhibitors, the enzyme complex concentration was lowered to 5 nM, and the assay duration was extended to 60 minutes, during which the time-dependence of product formation was linear.

Inhibition of CDK2/Cyclin a Retinoblastoma Kinase Activity

CDK2 was purified using published methodology (Rosenblatt et al., "Purification and Crystallization of Human Cyclin-dependent Kinase 2," *J. Mol. Biol.*, vol. 230, pp. 1317–1319 (1993)) from insect cells that had been infected with a baculovirus expression vector. Cyclin A was purified from *E. coli* cells expressing full-length recombinant cyclin A, and a truncated cyclin A construct was generated by limited proteolysis and purified as described previously (Jeffrey et al., "Mechanism of CDK activation revealed by the structure of a cyclin A-CDK2 complex," *Nature*, vol. 376, pp. 313–320 (Jul. 27, 1995). A complex of CDK2 and proteolyzed cyclin A was prepared and purified by gel filtration. The substrate for this assay was the same Rb substrate fragment used for the CDK4 assays, and the methodology of the CDK2/cyclin A and the CDK4/cyclin D3 assays was essentially the same, except that CDK2 was present at 150 nM or 5 nM. K$_i$ values were measured as described above.

The stimulation of cell proliferation by growth factors such as VEGF and others is dependent upon their induction of autophosphorylation of each of their respective receptor's tyrosine kinases. Therefore, the ability of a protein kinase inhibitor to block cellular proliferation induced by these growth factors is directly correlated with its ability to block receptor autophosphorylation. To measure the protein kinase inhibition activity of the compounds, the following constructs were used.

VEGF-R2 Construct for Assay

This construct determines the ability of a test compound to inhibit tyrosine kinase activity. A construct (VEGF-R2Δ50) of the cytosolic domain of human vascular endothelial growth factor receptor 2 (VEGF-R2) lacking the 50 central residues of the 68 residues of the kinase insert domain was expressed in a baculovirus/insect cell system. This construct is described by McTigue et al. in *Structure*, vol. 7, pp. 319–330 (1999) and co-pending U.S. patent application Ser. No. 09/390,326, filed Sep. 7, 1999. Of the 1356 residues of full-length VEGF-R2, VEGF-R2Δ50 contains residues 806–939 and 990–1171, and also one point mutation (E990V) within the kinase insert domain relative to wild-type VEGF-R2. Autophosphorylation of the purified construct was performed by incubation of the enzyme at a concentration of 4 $\mu$M in the presence of 3 mM ATP and 40 mM $MgCl_2$ in 100 mM Hepes, pH 7.5, containing 5% glycerol and 5 mM DTT, at 4° C. for 2 h. After autophosphorylation, this construct has been shown to possess catalytic activity essentially equivalent to the wild-type autophosphorylated kinase domain construct. See Parast et al., *Biochemistry*, vol. 37, pp. 16788–16801 (1998).

CHK 1 Construct for Assay

C-terminally His-tagged full-length human CHK1 (FL-CHK1) was expressed using the baculovirus/insect cell system. It contains 6 histidine residues (6xHis-tag) at the C-terminus of the 476 amino acid human CHK1. The protein was purified by conventional chromatographic techniques.

VEGF-R2 Assay

Coupled Spectrophotometric (FLVK-P) Assay

The production of ADP from ATP that accompanies phosphoryl transfer was coupled to oxidation of NADH using phosphoenolpyruvate (PEP) and a system having pyruvate kinase (PK) and lactic dehydrogenase (LDH). The oxidation of NADH was monitored by following the decrease of absorbance at 340 nm ($e_{340}$=6.22 $cm^{-1}$ $mM^{-1}$) using a Beckman DU 650 spectrophotometer. Assay conditions for phosphorylated VEGF-R2Δ50 (indicated as FLVK-P in the tables below) were the following: 1 mM PEP; 250 $\mu$M NADH; 50 units of LDH/mL; 20 units of PK/mL; 5 mM DTT; 5.1 mM poly($E_4Y_1$); 1 mM ATP; and 25 mM $MgCl_2$ in 200 mM Hepes, pH 7.5. Assay conditions for unphosphorylated VEGF-R2Δ50 (indicated as FLVK in the tables) were the following: 1 mM PEP; 250 $\mu$M NADH; 50 units of LDH/mL; 20 units of PK/mL; 5 mM DTT; 20 mM poly($E_4Y_1$); 3 mM ATP; and 60 mM $MgCl_2$ and 2 mM $MnCl_2$ in 200 mM Hepes, pH 7.5. Assays were initiated with 5 to 40 nM of enzyme. $K_i$ values were determined by measuring enzyme activity in the presence of varying concentrations of test compounds. The data were analyzed using Enzyme Kinetic and Kaleidagraph software.

ELISA Assay

Formation of phosphogastrin was monitored using biotinylated gastrin peptide (1–17) as substrate. Biotinylated phosphogastrin was immobilized using streptavidin coated 96-well microtiter plates followed by detection using anti-phosphotyrosine-antibody conjugated to horseradish peroxidase. The activity of horseradish peroxidase was monitored using 2,2'-azino-di-[3-ethylbenzathiazoline sulfonate(6)] diammonium salt (ABTS). Typical assay solutions contained: 2 $\mu$M biotinylated gastrin peptide; 5 mM DT; 20 $\mu$M ATP; 26 mM $MgCl_2$; and 2 mM $MnCl_2$ in 200 mM Hepes, pH 7.5. The assay was initiated with 0.8 nM of phosphorylated VEGF-R2Δ50. Horseradish peroxidase activity was assayed using ABTS, 10 mM. The horseradish peroxidase reaction was quenched by addition of acid ($H_2SO_4$), followed by absorbance reading at 405 nm. $K_i$ values were determined by measuring enzyme activity in the presence of varying concentrations of test compounds. The data were analyzed using Enzyme Kinetic and Kaleidagraph software.

CHK1 Assay

The production of ADP from ATP that accompanies phosphoryl transfer to the synthetic substrate peptide Syntide-2 (PLARTLSVAGLPGKK) was coupled to oxidation of NADH using phosphoenolpyruvate (PEP) through the actions of pyruvate kinase (PK) and lactic dehydrogenase (LDH). The oxidation of NADH was monitored by following the decrease of absorbance at 340 nm ($\in$340=6.22 $cm^{-1}$ $mM^{-1}$) using a HP8452 spectrophotometer. Typical reaction solutions contained: 4 mN PEP; 0.15 mM NADH; 28 units of LDH/ml; 16 units of PK/ml; 3 mM DTT; 0.125 mM Syntide-2: 0.15 mM ATP; 25 mM $MgCl_2$ in 50 mM TRIS, pH 7.5; and 400 mM NaCl. Assays were initiated with 10 nM of FL-CHK1. $K_i$ values were determined by measuring initial enzyme activity in the presence of varying concentrations of test compounds. The data were analyzed using Enzyme Kinetic and Kaleidagraph software.

Results of assays performed on compounds, which include the specific examples described above are provided below in Table I. Unless indicated otherwise in a particular entry, the units and assays used are as indicated in the applicable column of the table.

TABLE I

| | $K_i$ with CDKs | | | |
| Compd. | $K_i$ CDK4/D ($\mu$m) or Percent Inhibition | $K_i$ CDK2/A ($\mu$M) or Percent Inhibition | $K_i$ CHK1 ($\mu$M) or Percent Inhibition | $K_i$ VEGF ($\mu$M) or Percent Inhibition |
|---|---|---|---|---|
| A | 26.2 | 25.8 | | 10% inhibition at 5 $\mu$M |
| B | 3.1 | 6.2 | | 21% inhibition at 5 $\mu$M |
| C | 59 | 61 | 1.5 | |
| D | 7.4 | 25 | | |
| E | 9.7 | 22 | | |
| F | 25% inhibition at 10 $\mu$M | 37% inhibition at 10 $\mu$M | | |
| G | 10 | 10 | | |
| H | 3 | 3 | | |
| I | 4.7 | | | |
| J | 12 | 15 | 18 | |
| K | 4.7 | 6.3 | | |
| L | 5.3 | 2 | | |
| M | 4.1 | 21 | | |
| N | 4.9 | 2.4 | | |
| O | 1.6 | 0.062 | | |
| P | 2.1 | 0.11 | | |
| Q | 13% at 5 $\mu$M | 21% at 5 $\mu$M | | |
| R | 3.3 | 2.7 | 8% at 10 $\mu$M | |
| T | 2.1 | 3.2 | | |
| U | 2.3 | 0.08 | | |
| V | 12 | 0.27 | | |
| W | 0.9 | 0.016 | | |
| X | 12 | 0.39 | 1.8 | |

Inhibition of Cell Growth: Assessment of Cytotoxicity

Inhibition of cell growth was measured using the tetrazolium salt assay, which is based on the ability of viable cells to reduce 3-(4,5-dimethylthiazol-2-yl)-2,5-[2H]-diphenyltetrazolium bromide (MTT) to formazan (Mossman, Journal of Immunological Methods, vol.65, pp. 55–58(1983)). The water-insoluble purple formazan product was then detected spectrophotometrically. The HCT 116 cell line was grown in 96-well plates. Cells were plated in the appropriate medium at a volume of 135 $\mu$l/well in McCoy's 5A Medium. Plates were incubated for four hours before addition of inhibitor compounds. Different concentrations of inhibitor compounds were added in 0.5% (v/v) dimethylsulfoxide (15 $\mu$L/well), and cells were incubated at 37° C. (5% $CO_2$) for four to six days (depending on cell type). At the end of the incubation, MTT was added to a final concentration of 0.2 mg/mL, and cells were incubated for 4 hours more at 37° C. After centrifugation of the plates and removal of medium, the absorbance of the formazan (solubilized in dimethylsulfoxide) was measured at 540 nm. The concentration of inhibitor compound causing 50% inhibition of growth was determined from the linear portion of a semi-log plot of inhibitor concentration versus percentage inhibition. All results were compared to control cells treated only with 0.5% (v/v) dimethylsulfoxide.

TABLE II

| Example | HCT116 IC 50 ($\mu$M) | HCT116 IC 90 ($\mu$M) |
|---|---|---|
| O | 9.5 | 24 |
| W | 20 | |

The examples above illustrate compounds according to Formula I and assays that may readily be performed to determine their activity levels against the various kinase complexes. It will be apparent that such assays or other suitable assays known in the art may be used to select an inhibitor having a desired level of activity against a selected target.

The exemplary compounds described above may be formulated into pharmaceutical compositions according to the following general examples.

Example 1

Parenteral Composition

To prepare a parenteral pharmaceutical composition suitable for administration by injection, 100 mg of a water-soluble salt of a compound of Formula I is dissolved in DMSO and then mixed with 10 mL of 0.9% sterile saline. The mixture is incorporated into a dosage unit form suitable for administration by injection.

Example 2

Oral Composition

To prepare a pharmaceutical composition for oral delivery, 100 mg of a compound of Formula I is mixed with 750 mg of lactose. The mixture is incorporated into an oral dosage unit for, such as a hard gelatin capsule, which is suitable for oral administration.

While the invention has been illustrated by reference to specific and preferred embodiments, those skilled in the art will recognize that variations and modifications may be made through routine experimentation and practice of the invention. Thus, the invention is intended not to be limited by the foregoing description, but to be defined by the appended claims and their equivalents.

What is claimed is:

1. A compound of the Formula I:

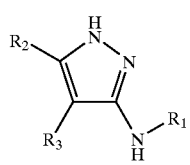

Formula I wherein:

$R_1$ is a substituted or unsubstituted aryl, heteroaryl, cycloalkyl, or heterocycloalkyl;

$R_2$ is a substituted or unsubstituted heteroaryl or heterocycloalkyl; and $R_3$ is hydrogen, fluorine, chlorine, bromine, iodine or a substituted or unsubstituted $C_{1-8}$ alkyl;

or a pharmaceutically acceptable salt of a compound of the Formula I.

2. A compound or pharmaceutically acceptable salt according to claim 1, wherein $R_1$ is unsubstituted or substituted phenyl, $R_2$ is substituted or unsubstituted heteroaryl, and $R_3$ is hydrogen.

3. A compound or pharmaceutically acceptable salt according to claim 1, wherein $R_1$ is unsubstituted phenyl or phenyl substituted with an electron-withdrawing group, $R_2$ is substituted or unsubstituted heteroaryl having at least one sulfur or nitrogen as a heteroatom, and $R_3$ is hydrogen.

4. A compound or pharmaceutically acceptable salt according to claim 1, wherein $R_1$ is phenyl substituted with an electron withdrawing group, $R_2$ is substituted or unsubstituted heteroaryl having at least one sulfur as a heteroatom, and $R_3$ is hydrogen.

5. A compound selected from the group consisting of

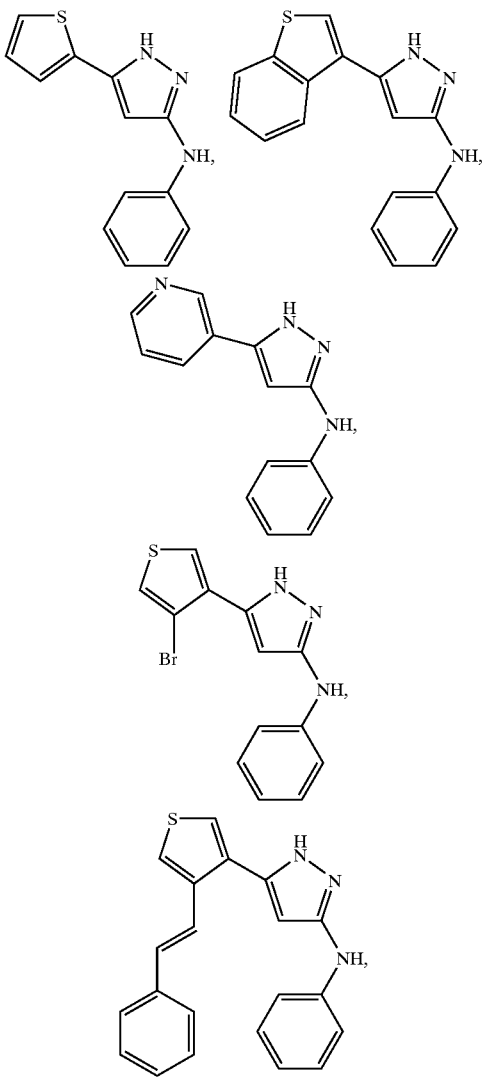

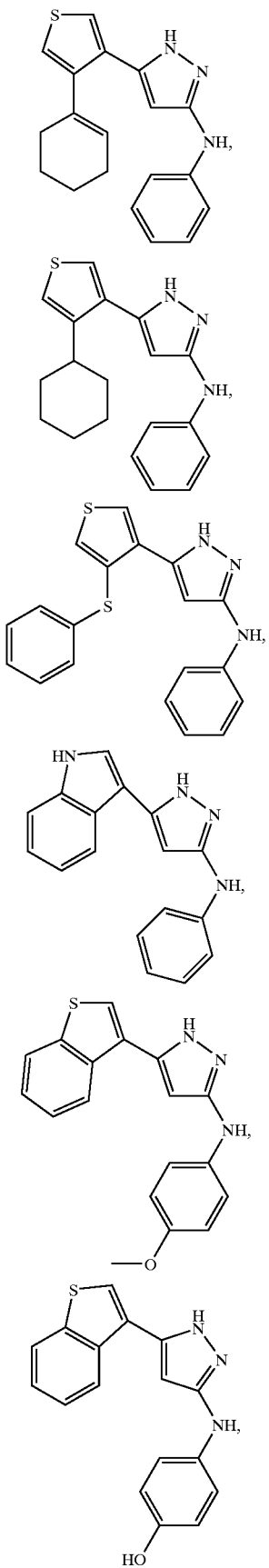
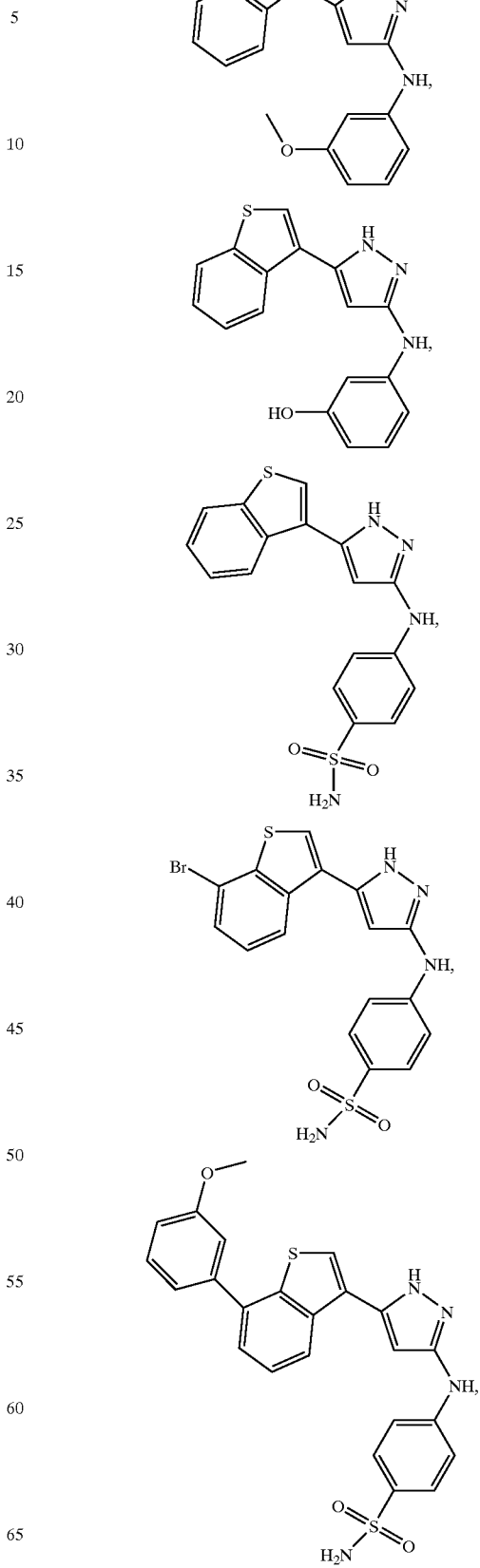

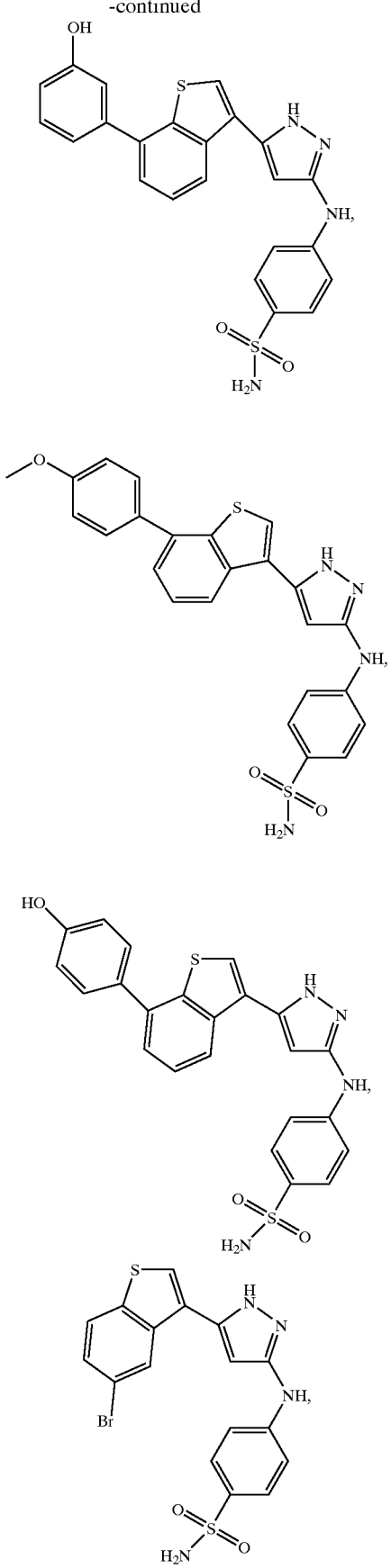

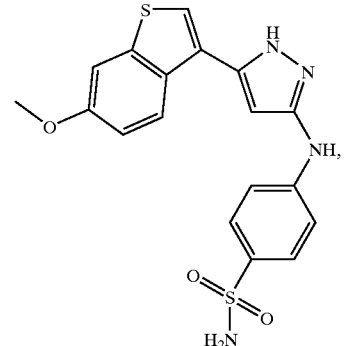

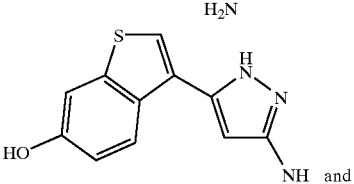

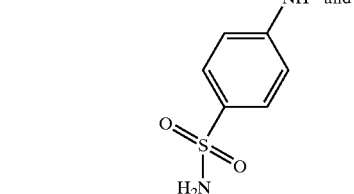

and

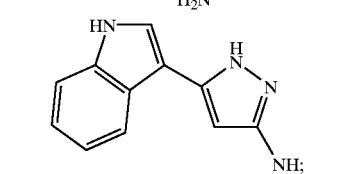

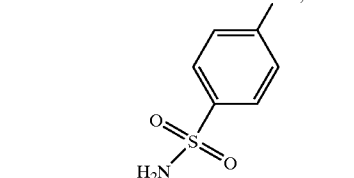

;

or a pharmaceutically acceptable salt of said comnpound.

6. A pharmaceutical composition comprising:

(a) an amount of a cell-cycle control agent effective to inhibit CDK4 or a CDK4/cyclin complex, said cell-cycle control agent being a compound of the Formula I:

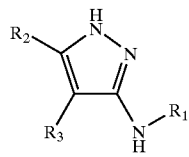

Formula I wherein:

$R_1$ is a substituted or unsubstituted aryl, heteroaryl, cycloalkyl, or heterocycloalkyl group;

$R_2$ is a substituted or unsubstituted heteroaryl or heterocycloalkyl; and $R_3$ is hydrogen, fluorine, chlorine, bromine, iodine or a substituted or unsubstituted $C_{1-8}$ alkyl;

or a pharmaceutically acceptable salt of a compound of the Formula I;

(b) a pharmaceutically acceptable carrier.

7. A method of treating a disease or disorder mediated by inhibition of CDK4 or a CDK4/cyclin complex, comprising administering to a subject in need of such treatment a cell-cycle control agent selected from the group consisting of: compounds according to Formula I:

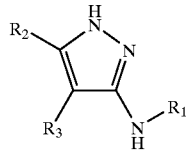

Formula I wherein:

$R_1$ is a substituted or unsubstituted alkyl, aryl, heteroaryl, cycloalkyl, or heterocycloalkyl;

$R_2$ is a substituted or unsubstituted heteroaryl or heterocycloalkyl; and $R_3$ is hydrogen, fluorine, chlorine, bromine, iodine or a substituted or unsubstituted $C_{1-8}$ alkyl;

pharmaceutically acceptable salts of compounds of the Formula I.

8. A pharmaceutical composition comprising:

(a) a therapeutically effective amount of a compound, or pharmaceutically acceptable salt of claim 1; and (b) a pharmaceutically acceptable carrier, diluent, vehicle or excipient therefor.

9. A method of treating a mammalian disease condition mediated by protein kinase activity, comprising administering to a mammal in need thereof a therapeutically effective amount of a compound according to Formula I:

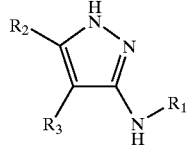

Formula I wherein:

$R_1$ is a substituted or unsubstituted alkyl, aryl, heteroaryl, cycloalkyl, or heterocycloalkyl;

$R_2$ is a substituted or unsubstituted heteroaryl or heterocycloalkyl; and $R_3$ is hydrogen, fluorine, chlorine, bromine, iodine or a substituted or unsubstituted $C_{1-8}$ alkyl;

or a pharmaceutically acceptable salt of a compound of the Formula I.

10. A method according to claim 9, wherein the mammalian disease condition is associated with tumor growth, cell proliferation, or angiogenesis.

11. A method of modulating or inhibiting the activity of a protein kinase receptor, comprising contacting the kinase receptor with an effective amount of a compound according to Formula I:

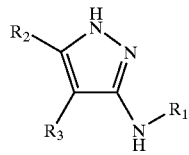

Formula I wherein:

$R_1$ is a substituted or unsubstituted alkyl, aryl, heteroaryl, cycloalkyl, or heterocycloalkyl;

$R_2$ is a substituted or unsubstituted heteroaryl or heterocycloalkyl; and $R_3$ is hydrogen, fluorine, chlorine, bromine, iodine or a substituted or unsubstituted $C_{1-8}$ alkyl;

or a pharmaceutically acceptable salt of a compound of the Formula I.

12. A pharmaceutical composition comprising:

(a) an effective amount for inhibiting a CDK or a CDK/cyclin complex of a cell-cycle control agent selected from:
(i) a compound of the Formula I according to claim 1:
(ii) a pharmaceutically acceptable salt of a compound of the Formula I; and (b) a pharmaceutically acceptable carrier.

* * * * *